(12) United States Patent
Imai et al.

(10) Patent No.: US 10,337,994 B2
(45) Date of Patent: Jul. 2, 2019

(54) SAMPLE LIQUID MEASURING DEVICE AND MEASURING METHOD

(71) Applicant: Kabushiki Kaisha Toshiba, Minato-ku, Tokyo (JP)

(72) Inventors: Kaita Imai, Tokyo (JP); Shouhei Kousai, Kanagawa (JP); Yosuke Akimoto, Kanagawa (JP); Michihiko Nishigaki, Kanagawa (JP); Yutaka Onozuka, Kanagawa (JP); Miyu Nagai, Kanagawa (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 15/695,377

(22) Filed: Sep. 5, 2017

(65) Prior Publication Data

US 2018/0080871 A1   Mar. 22, 2018

(30) Foreign Application Priority Data

Sep. 20, 2016  (JP) ................................. 2016-183168
Mar. 17, 2017  (JP) ................................. 2017-052988

(51) Int. Cl.
*G01N 21/65*  (2006.01)
*G01N 21/64*  (2006.01)
(Continued)

(52) U.S. Cl.
CPC ........... *G01N 21/645* (2013.01); *G01F 22/00* (2013.01); *G01F 23/292* (2013.01);
(Continued)

(58) Field of Classification Search
CPC ............... G01N 1/312; G01N 35/1002; G01N 2035/00138; G01N 35/00029;
(Continued)

(56) References Cited

U.S. PATENT DOCUMENTS 5,334,837 A     8/1994 Ikeda et al.
6,597,456 B2 *  7/2003 Kubo ................... G01N 21/553
                                                  250/239

(Continued)

FOREIGN PATENT DOCUMENTS

JP   5-99813 A     4/1993
JP   09-243558 A   9/1997

(Continued)

OTHER PUBLICATIONS

Makoto Watanabe et al., "Super Water Repellency of Vertically Aligned Single-Walled Carbon Nanotube Films," Proceedings of National Heat Transfer Symposium—The 43rd National Heat Transfer Symposium, http://www.photon.t.u-tokyo.ac.jp/~maruyama/papers/06/DS43_Watanabe.pdf, May 31-Jun. 2, 2006, 2 pages (w/Machine Translation).

(Continued)

*Primary Examiner* — Michael P Stafira
(74) *Attorney, Agent, or Firm* — White & Case LLP

(57) ABSTRACT

According to one embodiment, a measuring device for a sample liquid includes a container which stores the sample liquid, the container including a transparent or translucent optical component with an inclined surface to be brought into contact with the sample liquid, an optical sensor provided on a bottom of the container, which detects light from the sample liquid, and a measurement module which measures a concentration of a specific substance contained in the sample liquid, or a liquid height or liquid volume of the sample liquid based on a detected signal of the optical sensor.

20 Claims, 16 Drawing Sheets

(51) Int. Cl.
*G01F 23/292* (2006.01)
*G01F 22/00* (2006.01)
*G01N 21/03* (2006.01)

(52) U.S. Cl.
CPC ............... *G01N 2021/0382* (2013.01); *G01N 2021/6482* (2013.01); *G01N 2201/0638* (2013.01)

(58) Field of Classification Search
CPC ............ G01N 35/0099; G01N 35/025; G01N 15/1459; G01N 2035/1025; G01N 15/14; G01N 2015/1493; G01N 2035/00356; G01N 2035/0444; G01N 33/4925; G01N 35/0098; G01N 35/1011; G01N 35/1016; G01N 35/1079; G01N 11/00; G01N 11/02; G01N 11/06; G01N 13/02; G01N 15/12; G01N 1/2813; G01N 1/31; G01N 1/38; G01N 2013/0241; G01N 2015/1006; G01N 2015/1087; G01N 2015/1254; G01N 2015/1488; G01N 2021/3181; G01N 2021/434; G01N 2021/6482; G01N 2033/4975; G01N 2035/00079; G01N 2035/00168; G01N 2035/00376; G01N 2035/00534; G01N 2035/0494; G01N 2035/1006; G01N 2035/1034; G01N 2035/1037; G01N 21/314; G01N 21/4133; G01N 21/645; G01N 21/8507; G01N 2201/0638; G01N 33/02; G01N 33/48721; G01N 33/49; G01N 33/497; G01N 35/1004; G01N 35/1083; G01N 9/12; G02B 21/34; G02B 21/362; G02B 21/26; G02B 21/30; G02B 26/004; G02B 3/14; G02B 6/02395; G02B 6/272; G02B 6/287; G02B 7/028
See application file for complete search history.

(56) References Cited

U.S. PATENT DOCUMENTS

| | | | |
|---|---|---|---|
| 2009/0009757 A1* | 1/2009 | Mototsu | B01L 3/5082 356/246 |
| 2010/0038559 A1* | 2/2010 | Feke | G01N 21/6452 250/458.1 |
| 2010/0196206 A1 | 8/2010 | Lee et al. | |
| 2010/0225920 A1* | 9/2010 | Xia | B01L 9/06 356/442 |

FOREIGN PATENT DOCUMENTS

| | | |
|---|---|---|
| JP | 2002-310912 A | 10/2002 |
| JP | 2009-287999 A | 12/2009 |
| JP | 2010-531994 A | 9/2010 |
| JP | 5870439 B1 | 3/2016 |

OTHER PUBLICATIONS

"Preprocessing Tool for Microanalysis Pinpoint Concentration Plate," http://www.toray-research.co.jp/en/products/pinpoint_en.html, Jul. 14, 2017, 3 pages.

"Pinpoint Concentration Plate Manufactured by Toray Research Center," http://www.toray-research.co.jp/products/pinpoint.html, Jul. 14, 2017, 3 pages (w/Machine Translation).

* cited by examiner

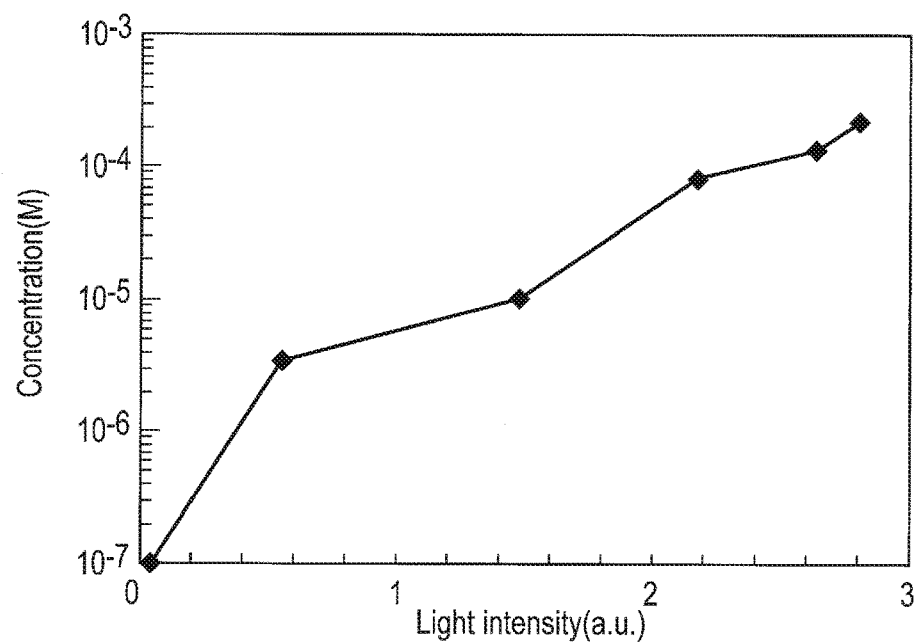
F I G. 5
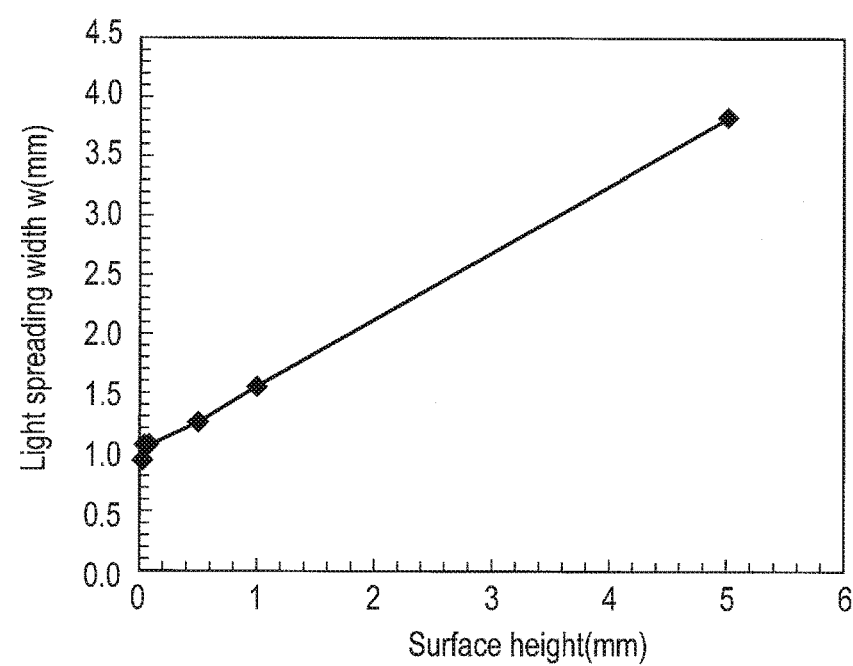
F I G. 6

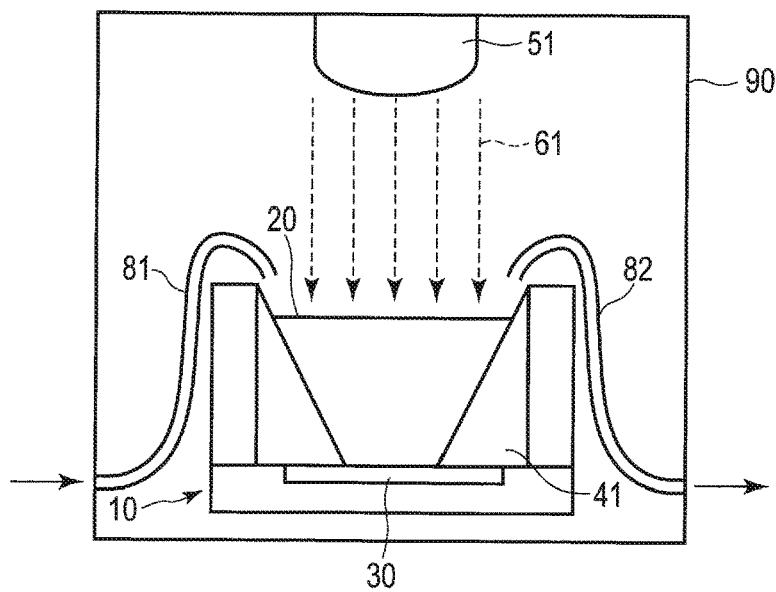
F I G. 9
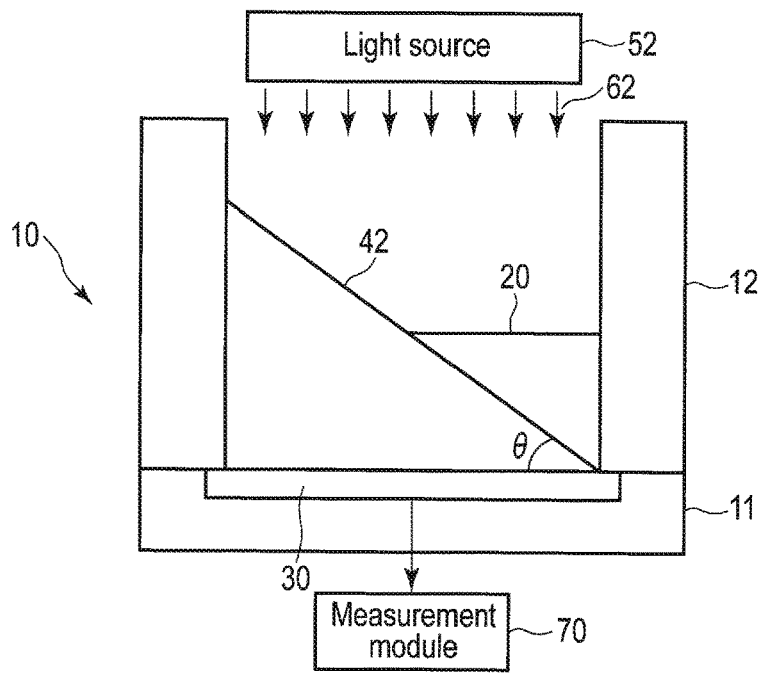
F I G. 10

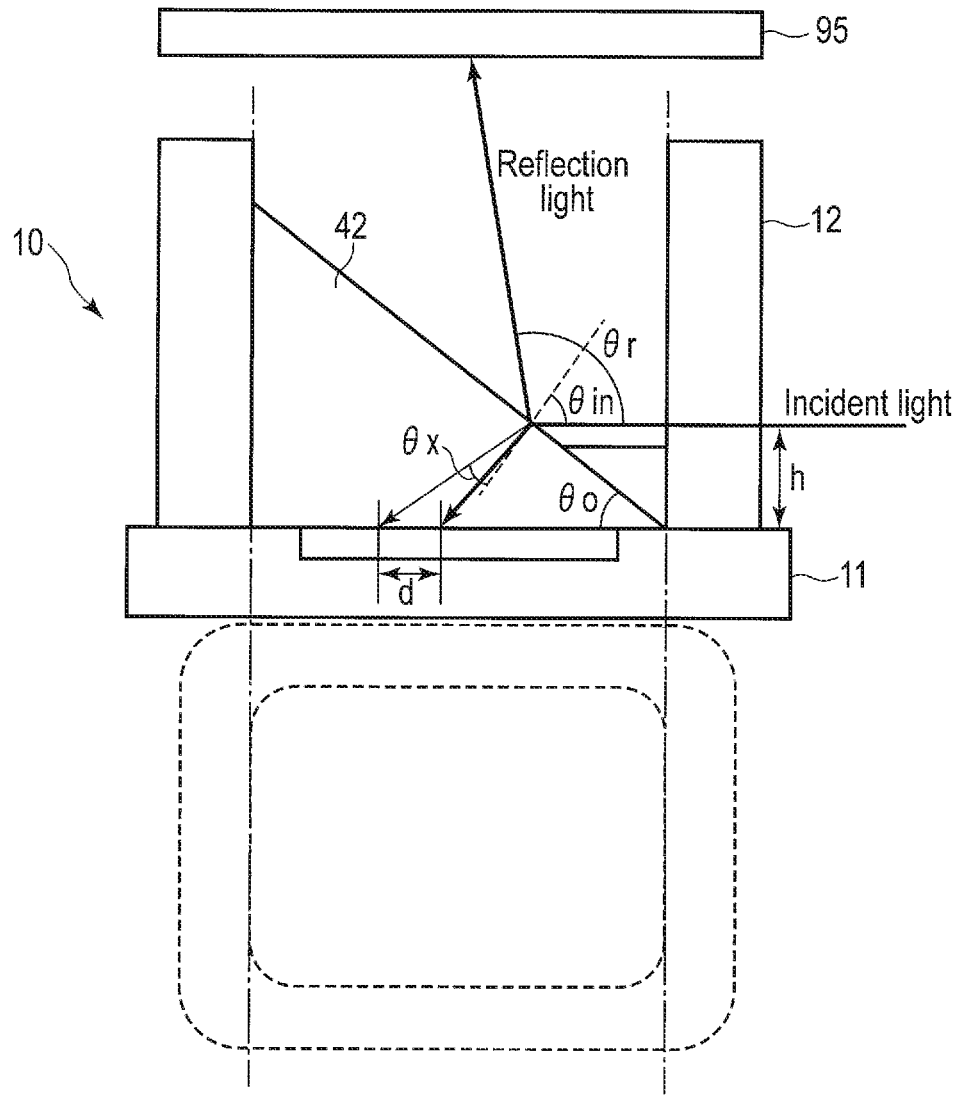
F I G. 15

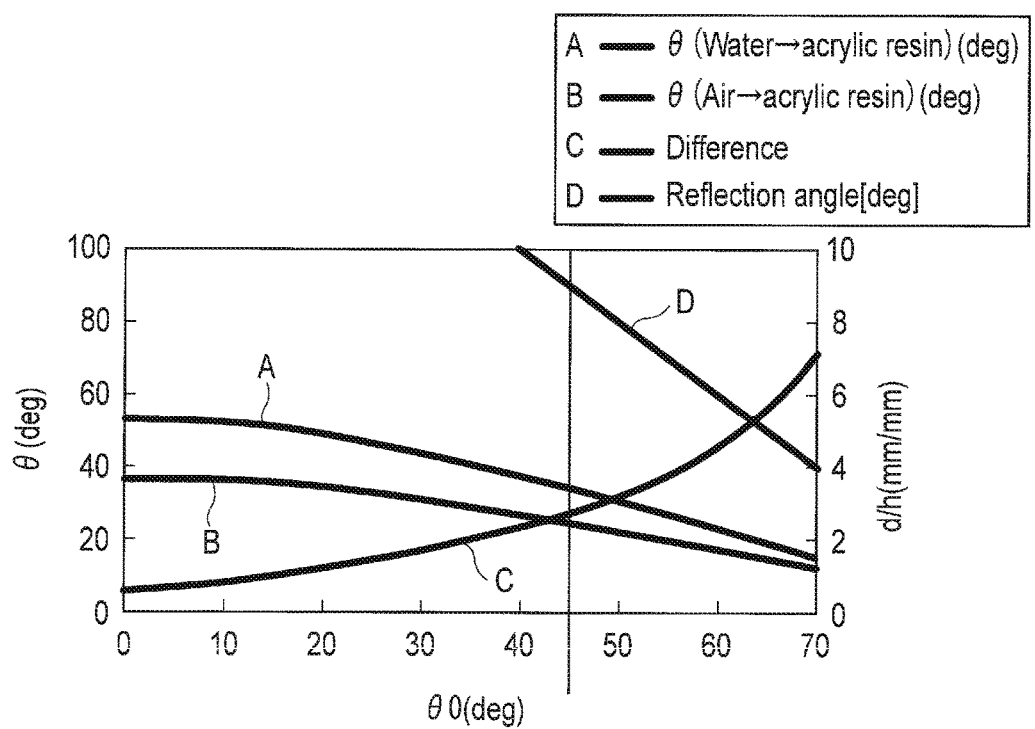
F I G. 16

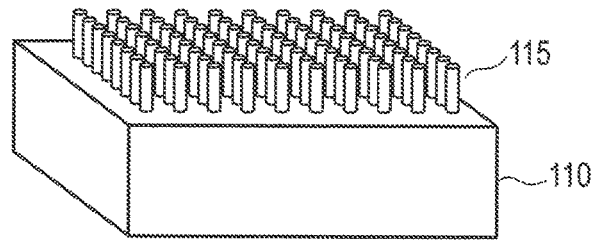
F I G. 22
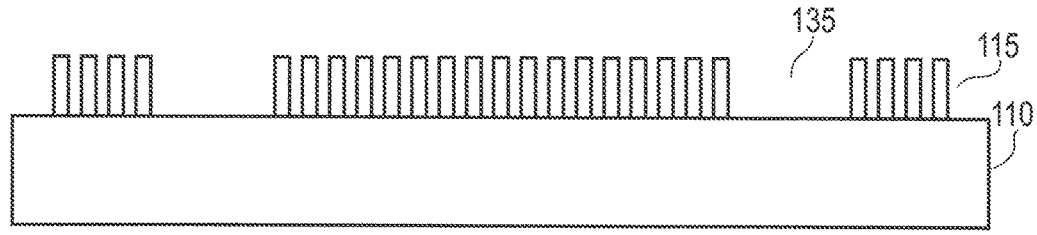
F I G. 23A
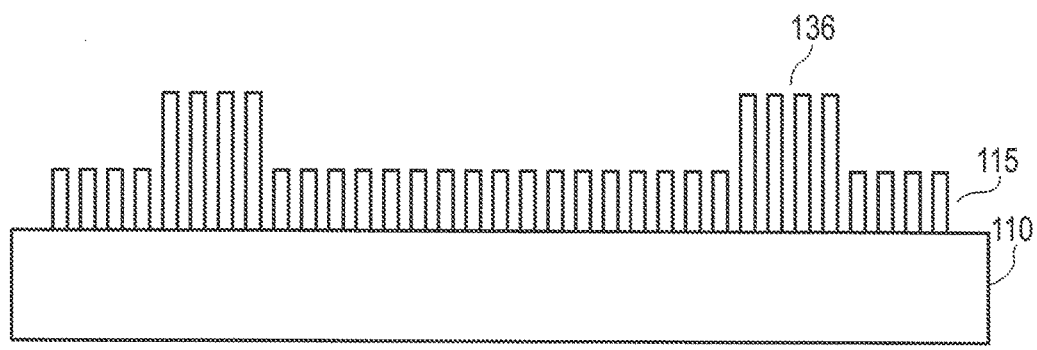
F I G. 23B

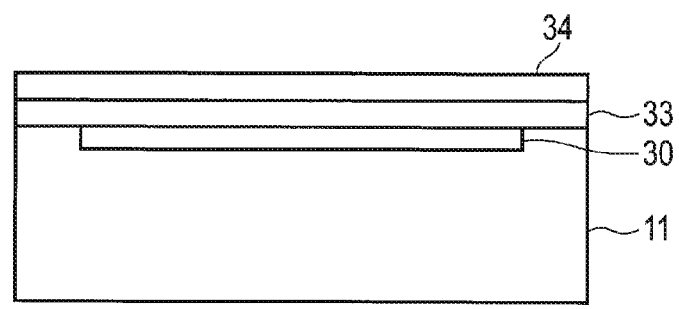
F I G. 27A
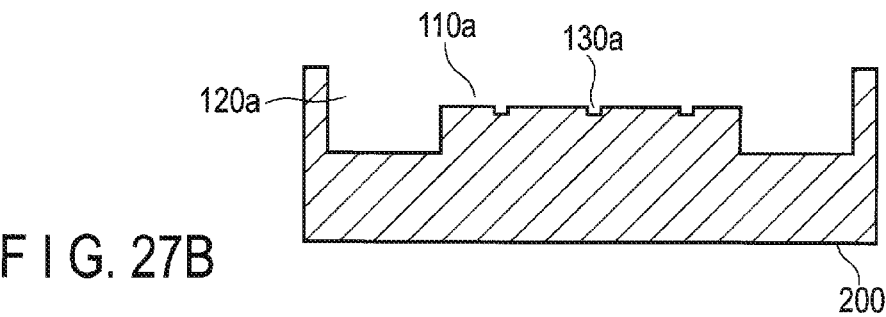
F I G. 27B
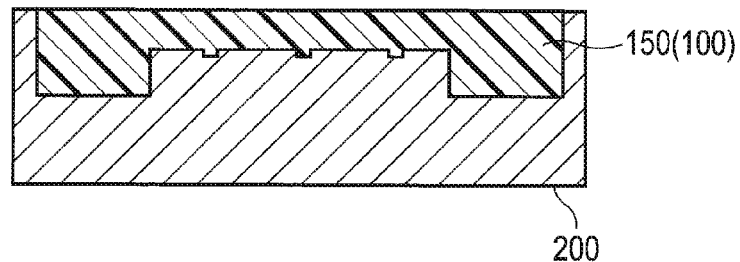
F I G. 27C
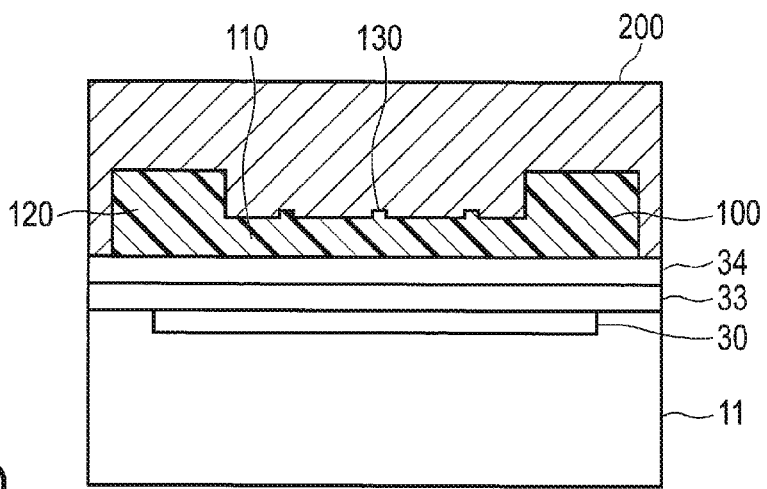
F I G. 27D

SAMPLE LIQUID MEASURING DEVICE AND MEASURING METHOD

CROSS-REFERENCE TO RELATED APPLICATIONS

This application is based upon and claims the benefit of priority from Japanese Patent Applications No. 2016-183168, filed Sep. 20, 2016; and No. 2017-052988, filed Mar. 17, 2017, the entire contents of all of which are incorporated herein by reference.

FIELD

Embodiments described herein relate generally to a sample liquid measuring device and a measuring method.

BACKGROUND

As a technique of detecting a specific substance contained in a sample liquid, a method of detecting fluorescent light from the specific substance is known. With this technique, if the amount of the substance contained is minute in orders of ppm to ppb, the quantity of light is so weak in some cases that the detection thereof may be difficult. Moreover, in the detection of a sample liquid, the fluid volume (liquid height) in a container needs to be measured in some cases. However, it is conventionally difficult to measure a fluid volume with precision especially, for example, when dropping a minute amount (1 mL or less) of liquid into a test container, due to dispersion in dropping fluid volume, evaporation of the solvent, or the like.

BRIEF DESCRIPTION OF THE DRAWINGS

FIG. 5 is a characteristic diagram showing the relationship between the intensity of the detected signal and the concentration of the sample liquid.

FIG. 6 is a characteristic diagram showing the relationship between the liquid height and the light spreading width.

FIG. 9 is a schematic structural diagram showing a sample liquid measuring device according to the second embodiment.

FIG. 10 is a schematic structural diagram showing a sample liquid measuring device according to the third embodiment.

FIG. 15 is a schematic structural diagram showing a sample liquid measuring device according to the fifth embodiment.

FIG. 16 is a characteristic diagram showing the relationship between the inclined angle 80 of the optical component, the refraction angle $\theta$, d/h and the reflection angle $\theta$.

FIG. 22 is a perspective view showing an example in which a water-repellent surface of periodic projections and recesses are formed on the surface of the bottom wall.

FIGS. 23A and 23B are cross sections each showing an example in which pinning patterns are provided in sections of the periodic projections and recesses.

FIGS. 27A to 27D are cross sections showing the manufacturing process of the measuring device of the seventh embodiment.

DETAILED DESCRIPTION

In general, according to one embodiment, there is provided a measuring device for a sample liquid comprising: a container which stores the sample liquid, the container including a transparent or translucent optical component with an inclined surface to be brought into contact with the sample liquid; an optical sensor provided on a bottom of the container, which detects light from the sample liquid; and a measurement module which measures a concentration of a specific substance contained in the sample liquid, or a liquid height or liquid volume of the sample liquid based on a detected signal of the optical sensor.

Hereafter, sample liquid measuring devices according to embodiments will now be described with reference to accompanying drawings.

First Embodiment

Figure 1:
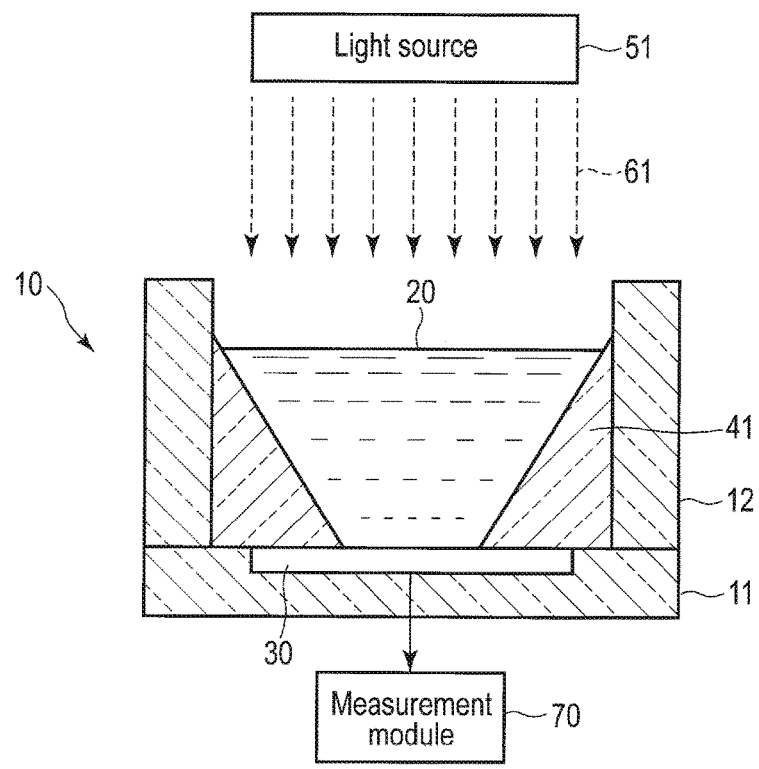
FIG. 1 is a schematic structural diagram showing a sample liquid measuring device according to the first embodiment.

FIG. 1 is a schematic structural diagram showing a sample liquid measuring device according to the first embodiment. The device measures the concentration of a specific substance in a sample liquid.

Reference number 10 in the figure illustrates a test container 10 including a substrate 11 and sidewalls 12 so as to store a sample liquid 20. The container 10 is formed from, for example, a transparent material such as glass or resin to include a rectangular or circular opening.

On the substrate 11, an optical sensor 30 which detects fluorescent light is provided. The optical sensor 30 is a two-dimensional photo sensor array, in which pixels are two-dimensionally arranged, and has spectral characteristics adjusted to be able to efficiently detect fluorescent light from the sample liquid 20. More specifically, the optical sensor 30 may be a CMOS or CCD image sensor manufactured as a semiconductor chip.

In the container 10, optical components 41 each formed from a transparent or translucent material and including a tapered side surface (slope) to be in contact with the sample liquid 20 are provided in right and left sides in the container 10, respectively. Each of the optical components 41 has a shape of, for example, a right triangular prism, and two perpendicular side surfaces are in contact with a side surface and a bottom surface of the container 10, respectively, and one remaining side surface is in contact with the sample liquid 20. Further, the optical components 41 are placed respectively on the right and left sides of the container. Note that the shape of the surface to be brought into the sample liquid is not limited to planer, but as long as the shape is known, a curvy or stepwise structure may be included. Thus, the substantial inner walls of the container 10 make a tapered form expanding upwards. With this structure, the evaporation of the solvent of the sample liquid 20 is promoted.

Note that when the opening of the container 10 is circular, the optical components 41 may form a ring shape having a tapered portion expanding upwards on its inner circumferential surface, whose upper opening is larger than the lower opening. Moreover, the sidewalls 12 and the optical component 41 may be formed as one body. That is, the sidewalls 12 may be formed into a structure including a slope on its inner side to impart the function of the optical component 41 to the sidewalls 12. In this case, the optical component 41 may be omitted.

A light source 51 which irradiates light into the sample liquid 20 is formed above the container 10. The light source 51 irradiates excitation light 61 from a perpendicular direction into the entire surface of the sample liquid 20, which excites the specific substance in the sample liquid 20 to emit fluorescent light. Moreover, the light source 51 may be a spectrum light source which outputs light of an arbitrary wavelength and may comprise optical components such as an optical filter which transmits a specific wavelength and a lens which collimated light beams. Here, the specific substance is a substance which generates fluorescent light by the irradiation of the excitation light 61 (the so-called fluorophore), or an entire aggregate of a substance to be detected and a fluorophore specifically bonded to the substance, or a fluorescent protein introduced by, for example, genetic engineering.

The fluorescent light from the specific substance is detected by the optical sensor 30. A detected signal of the optical sensor 30 is processed by a measurement module 70. The measurement module 70 measures the concentration of the specific substance contained in the sample liquid 20 based on the detected signal of the optical sensor 30. More specifically, the measurement module 70 includes, for example, a memory which stores a detected signal, a memory which stores the relationship between the intensity of the detected signal and the concentration of the specific substance, a memory which stores the relationship between the intensity of the detected signal and a liquid height, and a calculation circuit which calculates the liquid height of the sample liquid and the concentration of the specific substance in the sample liquid from the memory data stored in these various memories.

Figures 2A, 2B:
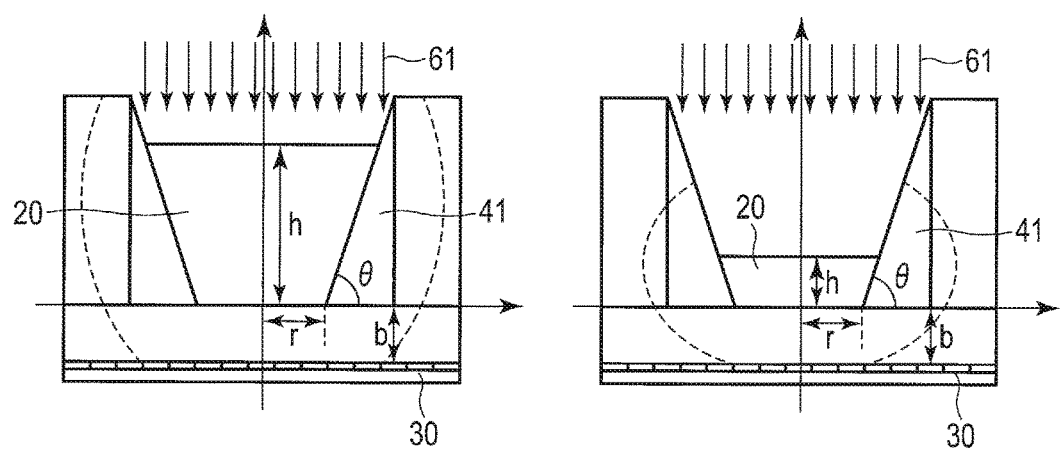
FIGS. 2A and 2B are schematic diagrams illustrating how light propagation to a sensor side differs depending on the liquid height of a sample liquid.

The liquid height (fluid volume) of the sample liquid 20 in the container 10 decreases due to concentration of the specific substance by the evaporation of the solvent, and thus the concentration increases (to be referred to as concentration due to evaporation). The intensity of the detected signal obtained with the optical sensor 30 differs from one case to another, where the liquid height is high as shown in FIG. 2A and the liquid height is low as shown in FIG. 2B. More specifically, when the liquid height is high, the signal intensity is low, whereas when the liquid height is low, the signal intensity is high. Further, the scope of the fluorescent light which reaches the optical sensor 30 through the optical component 41 differs depending on the liquid height. Therefore, as compared with the case where liquid height is low, the scope of the scattering light is large when the liquid height. Thus, as the liquid height is higher, the detected intensity of the optical sensor 30 becomes higher.

In FIGS. 2A and 2B, h represents the liquid height of the sample liquid 20, θ for the angle of inclination (for example, 60 degrees) of the optical component 41, r for the radius of the inner portion of the bank (for example, 0.05 mm), and b for the thickness of an interlayer (for example, 0.05 μm) formed on the surface of the optical sensor 30. Note that the interlayer is a protective layer which protects the surface of the sensor from the sample liquid and the like, and comprises one or more multilayered wiring layer which electrically controls the optical filter layer and photodiode to obtain desired spectral characteristics.

Figure 3:
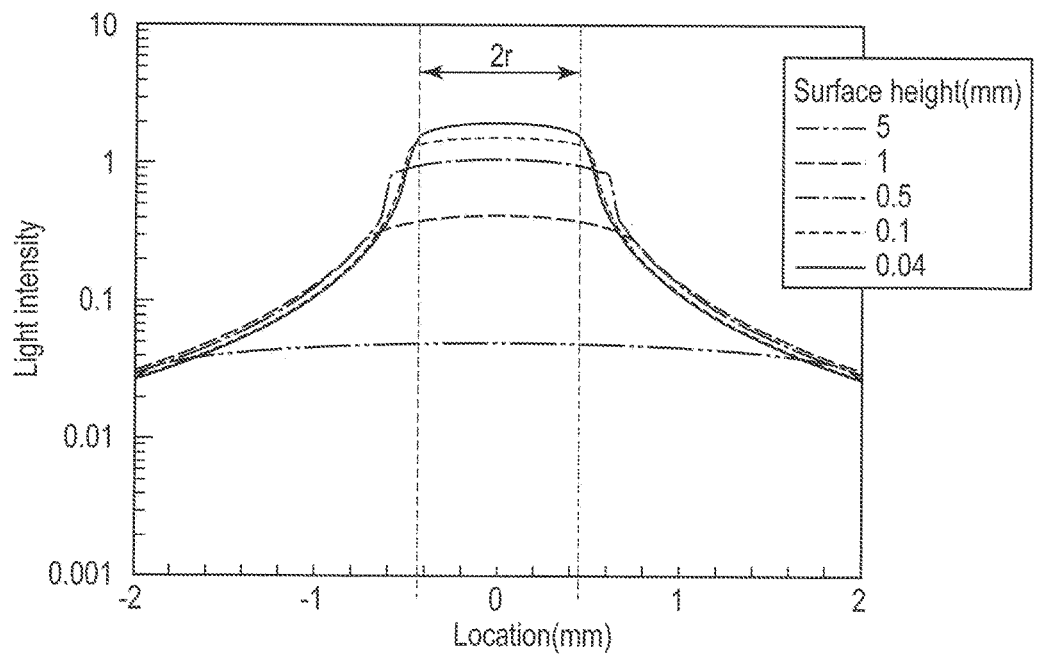
FIG. 3 is a characteristic diagram showing the relationship between the locations of pixels of the optical sensor and the intensity of a detected signal.

FIG. 3 is a characteristic diagram showing the relationship between the locations of pixels of the optical sensor 30 and the intensity of the detected signal. The intensity of the detected signal obtained with the optical sensor 30 is high in its central section of the graph and lower in its peripheral sections, and further the intensity of the detected signal becomes even higher in the central section as the liquid height is lower. Here, the signal intensity data in the central section corresponds to the concentration and the liquid height of a specific substance, and the inclination of the peripheral sections corresponds to the liquid height. That is, when the concentration of a specific substance is high, the signal intensity in the central section becomes high. Further, the profile of the intensity of the detected signal in the peripheral sections varies with the liquid height of the sample liquid 20. Note that the term "profile" used here indicates the distribution of the signal intensity values detected by the pixels of the optical sensor 30 and its change with the time.

Figure 4:
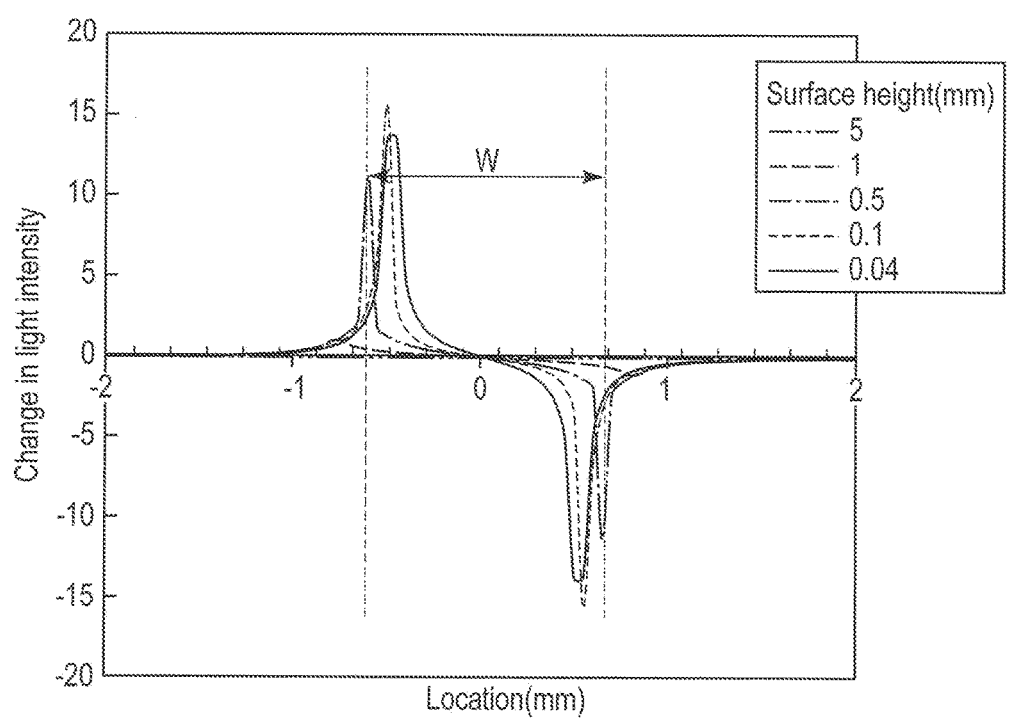
FIG. 4 is a characteristic diagram showing the relationship between the locations of pixels of the optical sensor and the change in the intensity of the detected signal.

FIG. 4 shows the results of differentiation of the signal intensity of FIG. 3, which indicates that a width W between the maximum and minimum of differentiation results (or difference) of the signal intensity with respect to the locations of the pixels differs depending on the liquid height. Therefore, the liquid height can be measured from W. In other words, the liquid height can be measured by calculating the width (W) of spreading of the fluorescent light from the variation in light intensity (differentiation in a planer direction).

FIG. 5 is a characteristic diagram showing the relationship between the intensity of the detected signal standardized in the central portion of the sensor and the concentration of the sample liquid 20. As shown, as the concentration of the specific substance in the sample liquid 20 is higher, the light intensity is higher. Meanwhile, FIG. 6 is a characteristic diagram showing the relationship between the liquid height of the sample liquid 20 and the width of spreading light. It is known from the figure that as the liquid height is higher, the width of spreading is greater.

Based on the above-described relationships, the relationship between the intensity of the detected signal standardized in the central portion of the sensor and the concentration is actually measured in advance by experiments using sample liquids whose concentrations are known. Then, a table which represents the relationship between the intensity of the detected signal and concentration is created, and stored on a memory in the measurement module 70. Thus, with reference to the table, the concentration can be calculated from the light intensity in the central portion of the sensor. Further, the relationship between the liquid height and the width of spreading light is actually measured in advance by experiments using sample liquids whose fluid volumes are known. Then, a table which represents the relationship between the liquid height and the width of spreading light is created and stored on a memory in the measurement module 70. Thus, with reference to the table, the liquid height can be calculated from the width W of spreading light.

Note that the signal intensity of the central portion of the sensor changes not only with the concentration of the specific substance in the sample liquid 20 but also with the liquid height (fluid volume). Here, the relationship between the signal intensity, liquid height and concentration is actually measured in advance by experiments using sample liquids of known concentrations and fluid volumes. By this way, it is possible to measure the concentration from the signal intensity of the optical sensor 30. More specifically, a table is created from the data shown in FIG. 5 for each liquid height and a table is created from the data shown in FIG. 6. Then, the liquid height is obtained from the detected signal of the optical sensor 30 and thus the concentration of the specific substance in the sample liquid 20 is obtained.

Moreover, the data used to create the tables may be acquired by the experimenter each time the experiment is carried out, or the tables created and acquired in advance may be written in the memory without acquiring data from each experiment, and used repeatedly. When the data are acquired from each experiment, fluctuations which may be created due to experimental environments including the temperature can be removed. When the data are written in the memory in advance, the experiment procedure for the experimenter can be simplified.

Figure 7:
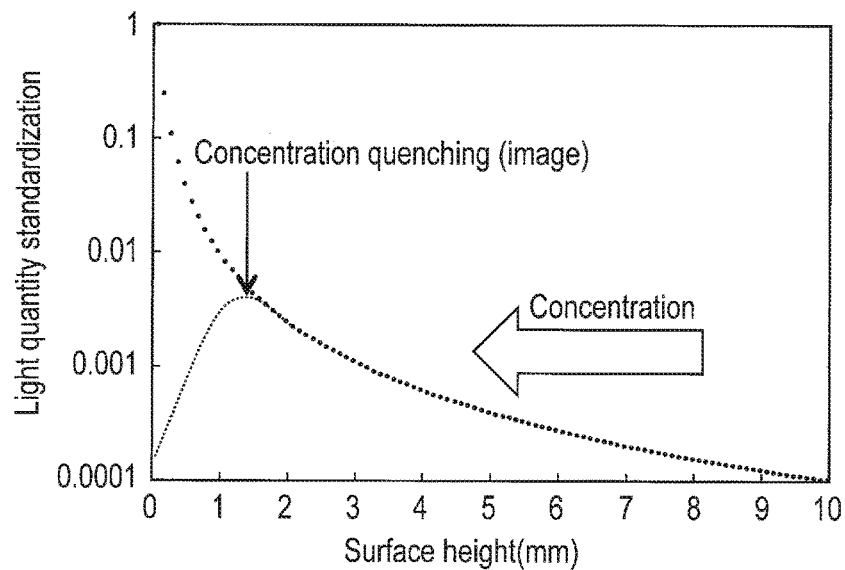
FIG. 7 is a characteristic diagram showing the relationship between the liquid height and the intensity of the detected signal.

It should be noted here that the sample liquid 20 is concentrated when the solvent evaporates. As the sample liquid 20 is concentrated, the liquid height of the sample liquid 20 lowers. As shown in FIG. 7, as the liquid height of the sample liquid 20 lowers, the quantity of light which reaches the optical sensor 30 increases, thereby enhancing the intensity of the detected signal. Therefore, in order to measure at high detection sensitivity, it is desirable that the sample liquid 20 should be concentrated. However, at the same time, if the sample liquid 20 is excessively concentrated, such a phenomenon may arise that the intensity of the detected signal significantly lowers (that is, the so-called concentration quenching). Because of these reasons, the measurement should desirably be repeated at predetermined intervals so that a chance of measurement should be obtained when the intensity of the detected signal is at maximum.

Figure 8:
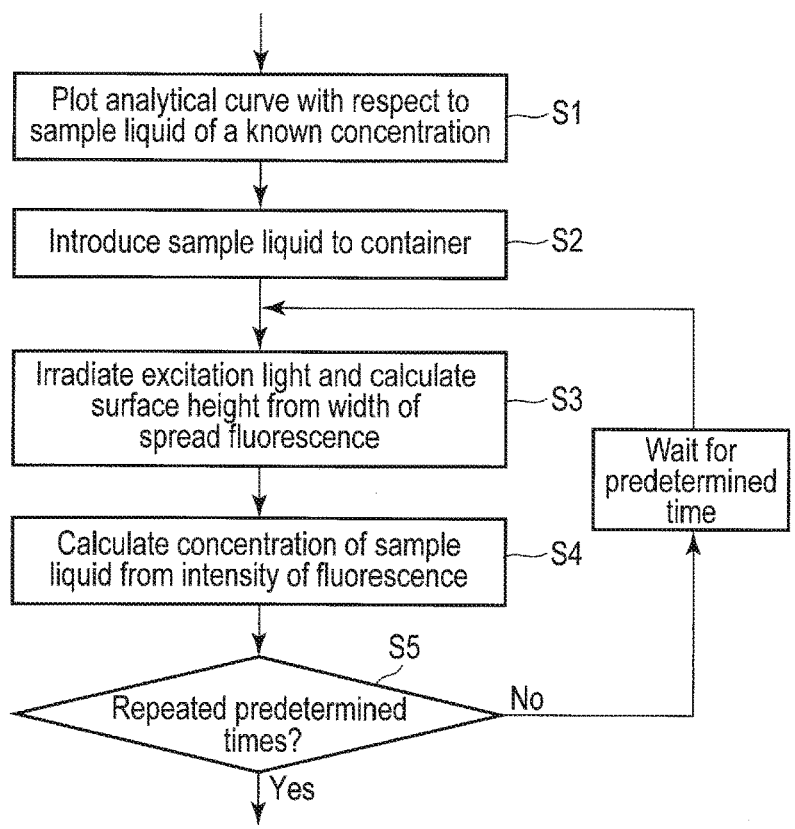
FIG. 8 is a flowchart illustrating a measurement procedure which uses the measuring device of the first embodiment.

Next, a measurement procedure using the measuring device of this embodiment will be described further with reference to the flowchart of FIG. 8.

First, an analytical curve with respect to the sample liquid 20 of a known concentration is plotted (S1). More specifically, an analytical curve which expresses the relationship of the concentration of a specific substance and the intensity of the detected signal as shown in FIG. 5 is plotted for each every liquid height (fluid volume), and is stored in the memory of the measurement module 70. Further, the analytical curve showing the relationship between the width of spreading fluorescent light and the liquid height shown in FIG. 6 is plotted, and stored in the memory of the measurement module 70.

Subsequently, only a fixed quantity of the sample liquid 20 is dropped into the container 10 to store the sample liquid 20 in the container 10 (S2). Here, since the frontage of the container 10 is large, the sample liquid 20 can be easily dropped into the container 10.

Next, the excitation light 61 is irradiated from the light source 51 to apply the excitation light 61 to the sample liquid 20 in the container 10. Thus, fluorescent light is generated from the sample liquid 20 by the exposure to the excitation light 61, which is then detected by the optical sensor 30. From the detected signal of the optical sensor 30, the liquid height of the sample liquid 20 is measured (S3). More specifically, the width W of spreading fluorescent light is obtained from the detected signal of the optical sensor 30, and from the spreading width W, the liquid height h of the sample liquid 20 is calculated out.

Subsequently, the concentration of the sample liquid 20 is measured from the data on the intensity of the detected signal of the optical sensor 30 (S4). More specifically, with reference to the analytical curve stored in the memory of the measurement module 70, the concentration of the sample liquid 20 is calculated out based on the intensity of the fluorescent light and the liquid height in the central portion of the optical sensor 30. Further, from the change in liquid height, the concentration of the sample liquid 20 before the concentration due to evaporation is calculated out.

Then, while the sample liquid 20 is concentrated by evaporation, steps S3 and S4 are repeated a plurality of times at a certain time interval (S5). The interval may be several tens of milliseconds, several minutes or several hours from and also may be changed in the middle of an experiment from the calculation result of the liquid height or concentration. Thus, it is expected to improve the sensitivity equivalently with the concentration. Moreover, before the phenomenon that the fluorescent light is weak due to an excessively high concentration (concentration quenching) occurs, the measurement can be finished.

Thus, according to the embodiment described above, the optical component 41 which includes a slope to be brought into contact with the sample liquid 20 is provided in the container 10 for storing a sample liquid and also the optical sensor 30 which detects fluorescent light is provided at the bottom of the container 10. With this structure, by irradiating the excitation light 61 to the entire surface of the sample liquid 20 dropped in the container 10 and two-dimensionally detecting the fluorescent light from the sample liquid 20 with the optical sensor 30, the liquid height (fluid volume) of the sample liquid 20 and the concentration of the specific substance in the sample liquid 20 can be measured at high precision.

Moreover, since the liquid height can be measured, the lowering of the liquid height can be measured at certain time intervals and thus the change in the degree of concentration of the sample liquid 20 can be also measured. Further, as shown in FIG. 7 described above, by utilizing the data on the relationship between the liquid height and the intensity data of the detected signal, the test can be carried out while the intensity of the detected signal is high. That is, it is possible to measure at high sensitivity. Thus, this embodiment is effective in detection of a substance contained in orders of, for example, ppm to ppb.

Second Embodiment

FIG. 9 is a schematic block diagram showing a sample liquid measuring device according to the second embodiment. Note that the same structural elements as those of FIG. 1 will be designated by the same reference symbols, and their detailed explanations will be omitted.

The second embodiment differs from the first embodiment in that a first nozzle (inlet mechanism) 81 to introduce a gas into the container 10 and a second nozzle (outlet mechanism) 82 to discharge the gas from the container 10 are provided above the container 10. The gas introduced to the container 10 may be air, or an air in which the $CO_2$ concentration is adjusted to a predetermined value (for example, 5%), or an inert gas such as argon and nitrogen.

Note that the container 10 may be accommodated in a sealed black box (measurement chamber) 90, or may be exposed to the air.

Thus, with the inlet/outlet mechanisms provided in addition to the structure of the first embodiment, not only an advantageous effect similar to that of the first embodiment is obtained, but also it becomes possible to control and accelerate the concentration of the sample liquid 20. Further, as an additional advantage, moisture condensation on the light source 51, which may occur when the sample liquid 20 is concentrated, can be prevented.

Third Embodiment

FIG. 10 is a schematic block diagram showing a sample liquid measuring device according to the third embodiment. Note that the same structural elements as those of FIG. 1 will be designated by the same reference symbols, and their detailed explanations will be omitted. This device is configured to measure the liquid height of the sample liquid 20.

In the container 10, an optical component 42 formed from a transparent or translucent material having a refractive index different from that of the sample liquid 20 is provided in the container 10. The optical component 42 has a shape of a triangular prism as in the case of the optical component 41 shown in FIG. 1, and two perpendicular side surfaces are in contact with a left side surface and a bottom surface of the container 10, respectively, and one remaining side surface is in contact with the sample liquid 20.

Note that it is sufficient if the optical component 42 is provided in at least one side of the container 10. The optical component 42 should preferably be of synthetic quartz, a transparent plastic such as polystyrene, or a transparent resin such as of acrylic. Further, it is desirable that the refractive index thereof greatly differ from that of the sample liquid 20. When the sample liquid 20 is an aqueous type, the refractive index is near 1.3 to 1.4. For example, the refractive index of synthetic quartz is 1.47 and the refractive index of polystyrene is 1.59.

The light source 52 is not necessarily be for excitation light, but may be for ordinary visible light. For example, a monochromatic light such as LED is desirable. The light source 52 is configured to irradiate the light 62 from a perpendicular direction in an area approximately the same as that of the opening of the container 10. Here, the incident light 62 should preferably be of collimated light in terms of a calculation model for simplification. The following descriptions will be provided on the assumption that the light 62 is collimated light. Moreover, the optical sensor 30 is not a fluorescent sensor but an ordinary photo-sensor which can detect the light from the light source 52, which is a two-dimensional array sensor.

Figure 11:
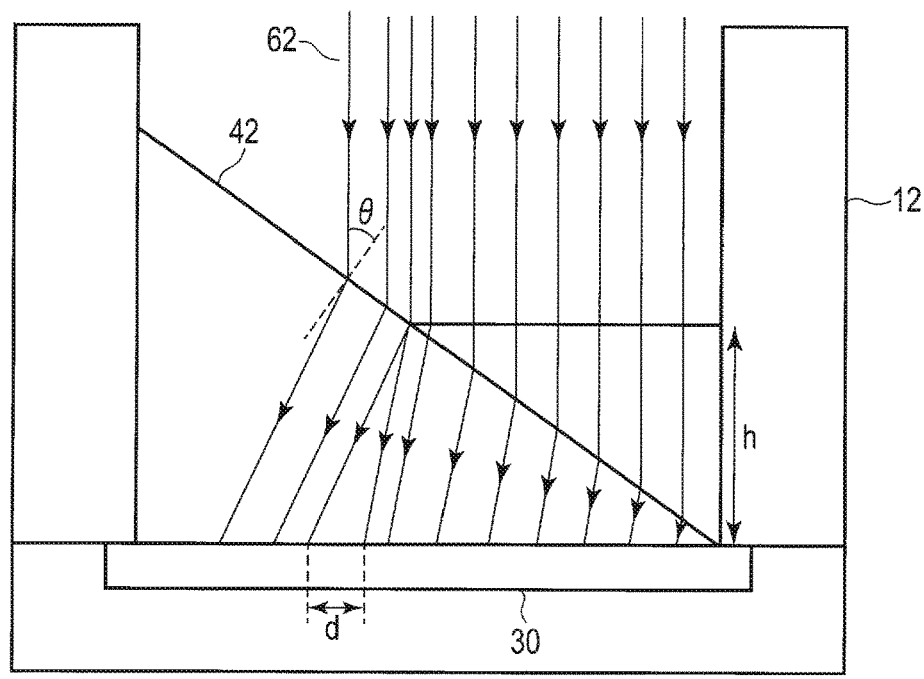
FIG. 11 is a schematic structural showing how incident light refracts in the third embodiment.

With this structure, when collimated light beam 62 is irradiated from above entirely into the container 10, the incident light (collimated light beam) 62 is refracted by the optical component 42 as shown in FIG. 11. Here, the light which enters the optical component 42 from the sample liquid 20 differs in angle of refraction from that entering the optical component 42 from the air. That is, since the difference in refractive index between the air and the optical component 42 and that between the sample liquid 20 and the optical component 42 differ from each other, and therefore the angle of refraction differs as well. Therefore, in the plane of the optical sensor 30 of the incident light, the location of the light entering the optical component 42 from the air shifts by only d with respect to that of the light entering the optical component 42 from the sample liquid 20.

Figure 12A:
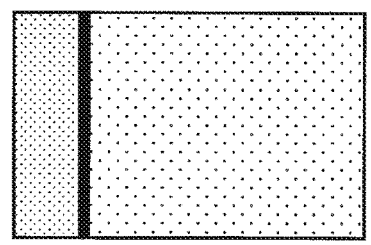
FIGS. 12A and 12B are diagrams showing an image and a gradation value obtained by the optical sensor.
Figure 12B:
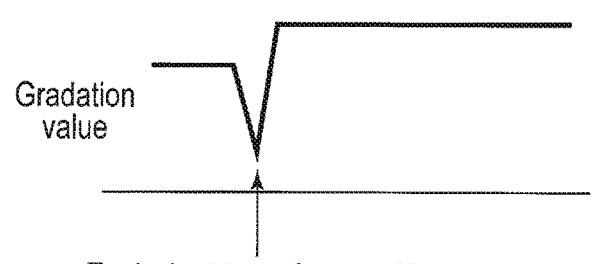

Thus, the detected signal of the optical sensor 30 becomes extremely low near the interface of the sample liquid 20 as illustrated by an image obtained with the optical sensor 30 in FIG. 12A and the gradation value of the detected signal shown in FIG. 12B. This location is determined to correspond to the interface of the sample liquid 20. In this manner, it becomes possible to measure the liquid height of the sample liquid 20 from the detected signal of the optical sensor 30.

Figure 13:
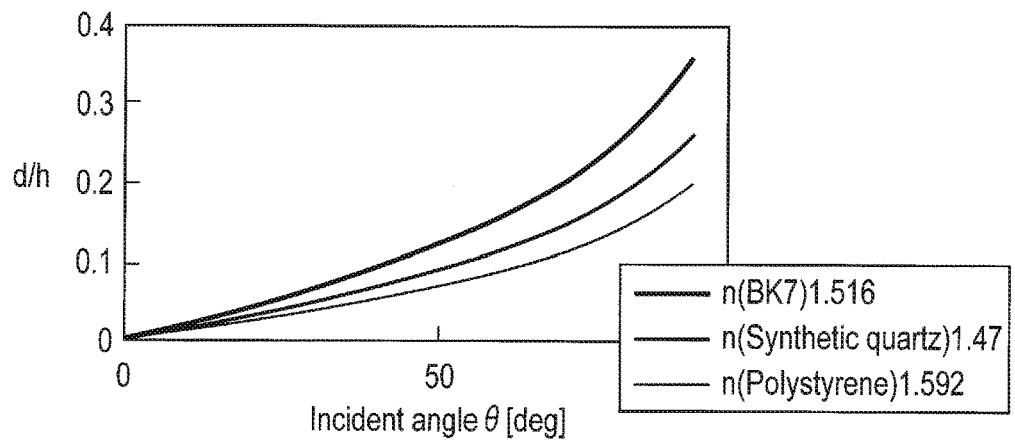
FIG. 13 is a characteristic diagram showing the relationship between a light incident angle $\theta$, and a value d/h.

Here, when the amount of shift of the incident position in the surface of the optical sensor 30 is expressed by d and the height of the surface is expressed by h, d/h becomes greater as the angle of incidence $\theta$ is larger, and further as the refractive index of the optical component 42 is greater, as shown in FIG. 13. Therefore, as the optical component 42, it is desirable to use a material with high refractive index such as polystyrene.

Thus, according to this embodiment, the optical component 42, which has a refractive index different from that of the sample liquid 20, is placed in the container 10 and light is irradiated entirely from above the container 10 and light transmitting the optical component 42 is detected with the optical sensor 30. In this manner, the liquid height of the sample liquid 20 can be measured at high precision. That is, by utilizing the refraction of light, the volume of the sample liquid 20 can be measured at high accuracy.

Fourth Embodiment

Figure 14:
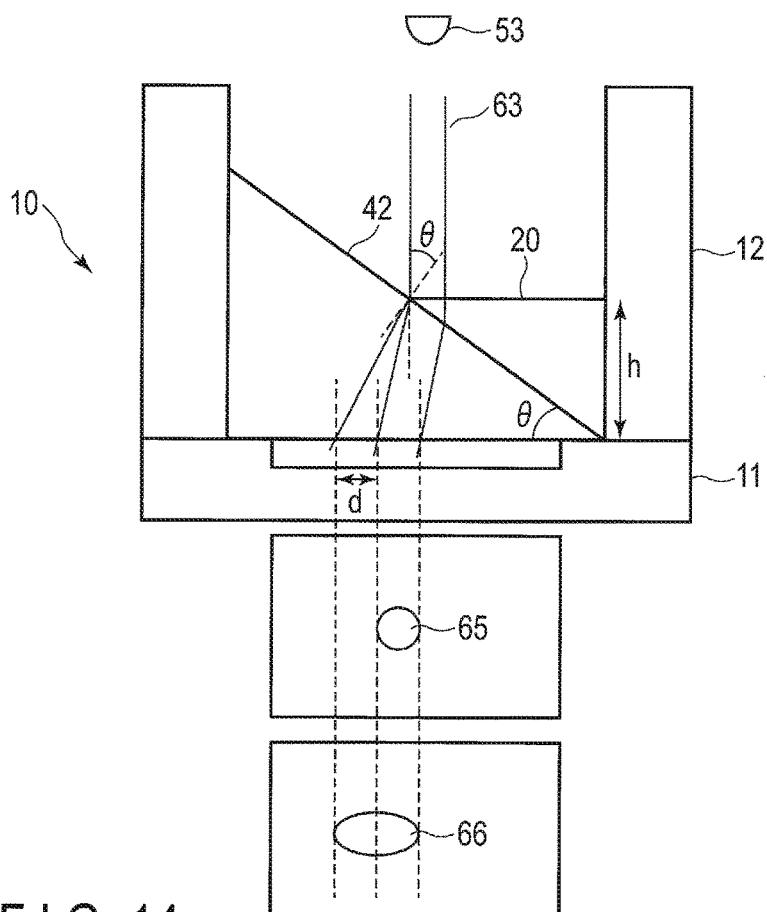
FIG. 14 is a schematic structural diagram showing a sample liquid measuring device according to the fourth embodiment.

FIG. 14 is a schematic block diagram showing a sample liquid measuring device according to the fourth embodiment. Note that the same structural elements as those of FIG. 10 will be designated by the same reference symbols, and their detailed explanations will be omitted.

The fourth embodiment is different from the third embodiment in that fine spot light 63 is irradiated in place of irradiating light entirely. More specifically, a light source 53 is configured to irradiate the spot light 63 from a perpendicular direction into the container 10. Further, the light source 53 can be scanned horizontally (a direction collimated to the array surface of the optical sensor 30).

In this embodiment, the difference in refractive index between the sample liquid 20 and the optical component 42 differs from that between the air and the optical component 42. Due to this difference, the angle of refraction of light entering the optical component 42 from the sample liquid 20 differs from that of the light entering the optical component 42 from the air. Therefore, as in the third embodiment, the location of the light entering the optical component 42 from the air shifts by only d with respect to that of the light entering the optical component 42 from the sample liquid 20 in the incident plane of the optical sensor 30.

When the spot light 63 is irradiated on a right side of the interface of the sample liquid 20, a spot image 65 obtained by the optical sensor 30 has a spot diameter approximately the same as that of the incident spot light 63. On the other hand, when the spot light 63 is irradiated near the interface of the sample liquid 20, a spot image 66 obtained by the optical sensor 30 expands to right and left as compared to the spot diameter of the incident spot light 63. In other words, near the interface of the sample liquid 20, the shape of the spot image detected by the optical sensor 30 greatly changes. In this manner, it can be determined from the spot image detected with the optical sensor 30 that the liquid now has a certain liquid height.

Further, by horizontally scanning the spot light 63 by the light source 53, it is possible to measure an arbitrary liquid height of the sample liquid 20. Furthermore, when the sample liquid 20 is dropped in the container 10 while irradiating the spot light 63 to a surface position to be set, and then the dropping is stopped at the position where the spot image becomes large, it is possible to introduce the sample liquid 20 to a determined height.

Thus, according to this embodiment, the optical component 42, which has a refractive index different from that of the sample liquid 20, is placed in the container 10, and the spot light 63 is irradiated from above the container 10 and light transmitting the optical component 42 is detected with the optical sensor 30. In this manner, the liquid height of the sample liquid 20 can be measured at high precision. That is, by utilizing the refraction of light, the volume of the sample liquid 20 can be measured at high accuracy.

Fifth Embodiment

FIG. 15 is a schematic block diagram showing a sample liquid measuring device according to the fifth embodiment. Note that the same structural elements as those of FIG. 10 will be designated by the same reference symbols, and their detailed explanations will be omitted.

The structure of the fifth embodiment is substantially the same as that shown in FIGS. 10 and 14 except that light is irradiated not from above the container 10, but from a horizontal direction. That is, the light source is provided in a side in place of above the container 10 though not shown in the figure. Moreover, a material which transmits light (such as glass or polystyrene) is used for the sidewall. Note that the figure also illustrates various structural bodies 95 located above the container 10.

In the fifth embodiment also, the angle of refraction of light entering the optical component 42 from the sample liquid 20 differs from that of the light entering the optical component 42 from the air. The irradiating light may be of an entire surface irradiation as in the third embodiment, or spot irradiation as in the fourth embodiment.

In the case of entire surface irradiation, the liquid height of the sample liquid 20 can be calculated from the value of the gradation of the detected signal of the optical sensor 30 as shown in FIG. 12 described above. On the other hand, in the case of spot irradiation, the liquid height of the sample liquid 20 can be calculated from the shape of the spot image obtained with the optical sensor 30.

FIG. 16 shows an example of the characteristic diagram showing the relationship between the angle of inclination of the optical component 42, the angle of refraction, the angle of reflection and the amount of shift. The horizontal axis indicates the angle of inclination θ0 of the optical component 42, the left-hand side vertical axis for the refraction angle and reflection angle θ, and the right-hand side vertical axis for the amount of shift d/h in the location in the sensor.

The refraction angle of the light entering the optical component 42 from the sample liquid 20 is represented by A, the refraction angle of the light entering the optical component 42 from the air is represented by B, the difference in amount of shift between A and B is represented by C, and the reflection angle in the optical component 42 is represented by D.

As the angle of inclination θ0 of the optical component 42 is greater, the refraction angle θ becomes less. As the angle of inclination θ0 of the optical component 42 is greater, the amount of shift d/h becomes larger. As the angle of inclination θ0 of the optical component 42 is greater, the angle of reflection 8 becomes smaller, and when the angle of inclination θ0 is 45 degrees, the reflection angle is 90 degrees.

As described above, also in this embodiment, the liquid height of the sample liquid 20 can be measured with high precision. Here, it is preferable to set the angle of inclination of the optical component 42 to 45 degrees, since in this case, the reflection light is entirely directed perpendicularly. To explain, the primary reflection light reflected by the optical component 42 is directed towards the structural bodies 95, but if the reflection light enters to the structural bodies 95 at an angle other than right angles, the secondary reflection light in the structural bodies 95 is reflected at an angle different from that of the incident light (the primary reflection light). That is, the secondary reflection light results in stray light, which may desirably cause an error in the measurement. When the angle of inclination is 45 degrees, the secondary reflection light follows the same light path as that of the primary reflection light in a reverse direction, that is, the secondary reflection light does not results in stray light. Note that it is preferable to subject the location of the incident of the primary reflection light in the structural bodies 95 to a low-reflection processing, for example, by applying black alumite or black resin.

Sixth Embodiment

Figure 17:
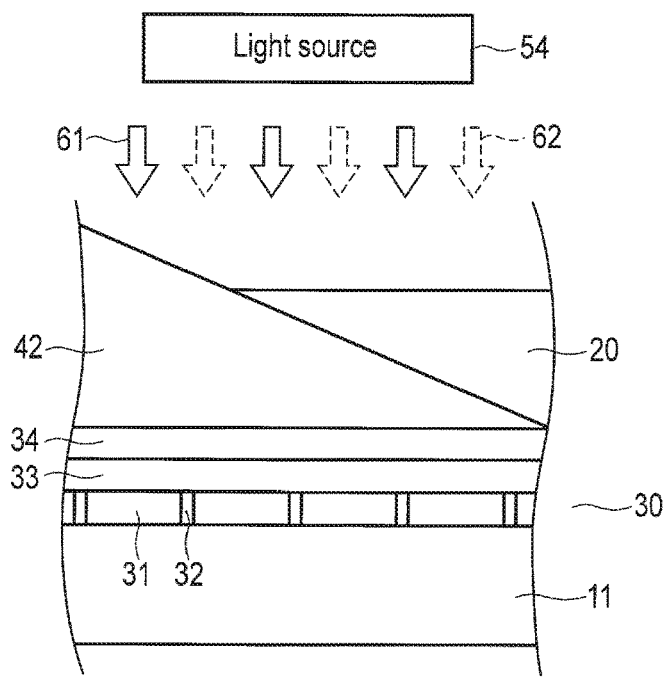
FIG. 17 is a cross section showing a main structure of a sample liquid measuring device according to the sixth embodiment.

FIG. 17 is a sectional view showing the main structure of a sample liquid measuring device according to the sixth embodiment. Note that the same structural elements as those of FIG. 10 will be designated by the same reference symbols, and their detailed explanations will be omitted. This device is configured to measure the liquid height and the concentration of the sample liquid 20.

The basic structure is similar to that of the third embodiment, but the light source 54 is configured to switch the wavelength of emission light, more specifically, for example, to switch between excitation light 61 and collimated light beam 62 of wavelength different from that of the excitation light 61. The optical sensor 30 can detect the fluorescent light by the excitation light 61 and the collimated light beam 62, respectively.

Figure 18:
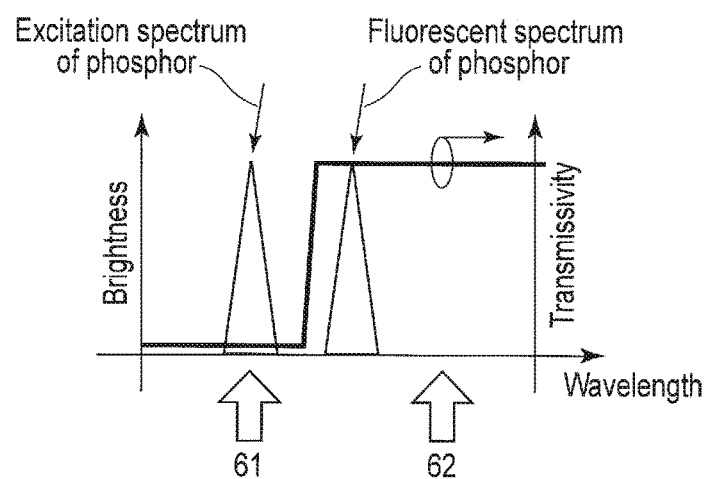
FIG. 18 is a schematic diagram illustrating the relationship between the spectra of excitation light and fluorescent light, and the transmittance of the filter.

The figure illustrates pixels 31 of the optical sensor 30, insulators 32 which separate the pixels 31 from each other, a protective insulating layer 33 which protects the pixels 31, and an optical filter 34. Note that the protective insulating layer 33 may contain one or more wiring layer which controls the pixels in the integrated circuit. The optical filter 34 is configured to pass the light having a wavelength longer than that of the excitation light 61 as shown in FIG. 18. That is, the transmittance to the excitation light 61 is low, and the transmittance to a wavelength longer than that is high. Note that as the optical filter 34, a dielectric multilayer filter, an organic absorption filter, a plasmon filter or the like can be used.

Therefore, when the excitation light 61 is irradiated from the light source 54, the optical sensor 30 can detect the hardly reduced excitation light 61 but detects fluorescent light emitted from the fluorophores. On the other hand, when the collimated light beam 62 is irradiated from the light source 54, the irradiated light itself is detected by the optical sensor 30.

Figure 19:
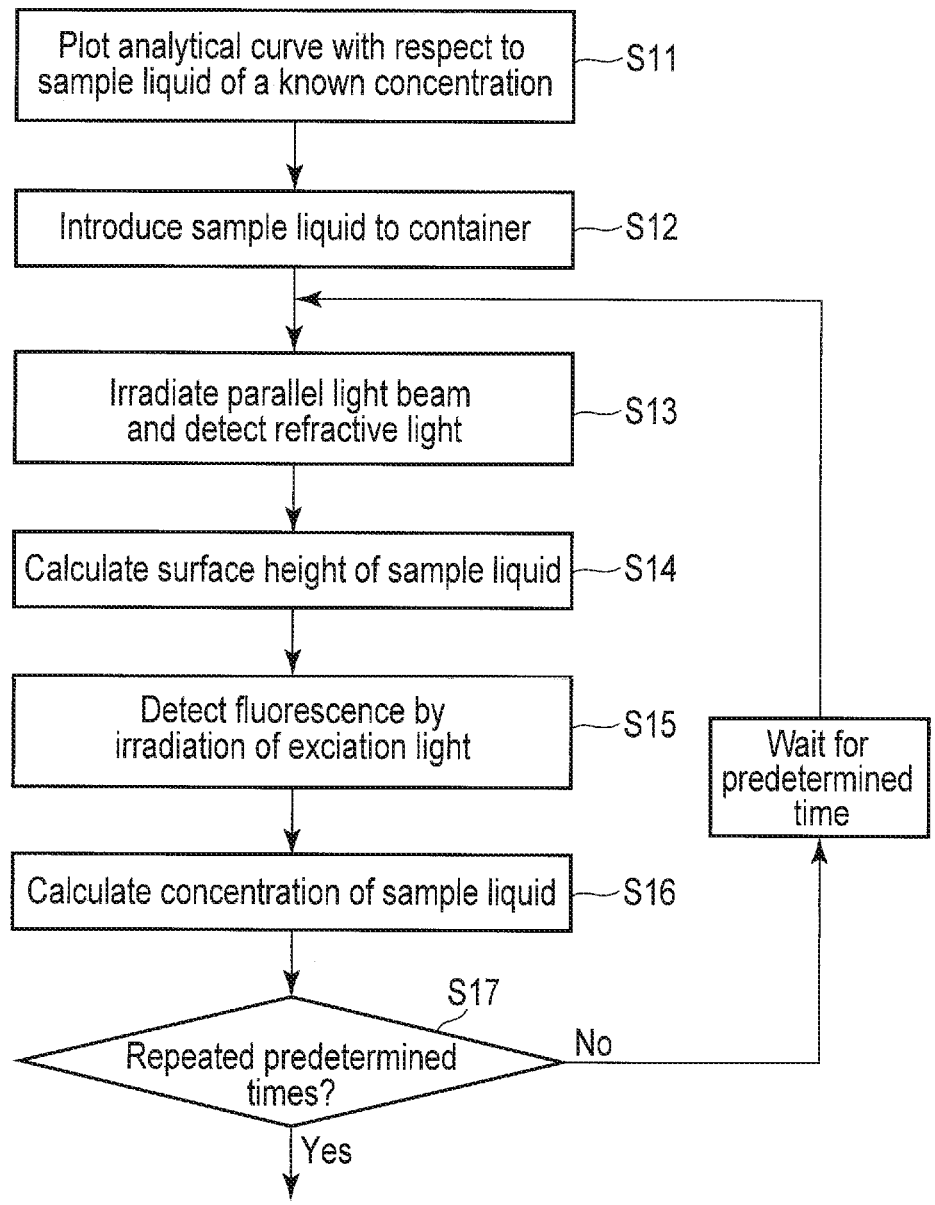
FIG. 19 is a flowchart illustrating a measurement procedure which uses the measuring device of the sixth embodiment.

Next, a measurement procedure using the measuring device of this embodiment will be further described with reference to the flowchart of FIG. 19.

First, an analytical curve with respect to the sample liquid 20 of a known concentration is plotted (S11). Subsequently, only a fixed quantity of the sample liquid 20 is dropped into the container 10 to store the sample liquid 20 in the container 10 (S12). Up to this step, the process is the same as that of the flowchart of FIG. 8.

Next, the collimated light 62 is irradiated from the light source 54 (S13). Then, the liquid height is calculated out from the detected signal of the optical sensor 30 (S14). That is, the liquid height of the sample liquid 20 is calculated out from the image as shown in FIG. 12A described above, or the gradation value as shown in FIG. 12B described above.

Subsequently, the excitation light 61 is irradiated from the light source 54, and the excitation light 61 is irradiated to the sample liquid 20 in the container 10. The optical sensor 30 detects the fluorescent light generated in the sample liquid 20 by the irradiation of the excitation light 61 (S15). Then, the concentration of the sample liquid 20 is calculated out from the detected signal of the optical sensor 30 (S16). More specifically, based on the intensity of fluorescent light obtained with the optical sensor 30 and the liquid height, the concentration of the sample liquid 20 is calculated out and also the concentration of the sample liquid 20 before concentration due to evaporation is calculated out with reference to the data of the analytical curve stored in the memory of the measurement module 70.

Then, while concentrating the sample liquid 20 by evaporation, steps S13 to S16 are repeated a plurality of times (S15). By repeating the steps, it is expected to improve the sensitivity equivalently with the concentration. Moreover, before the phenomenon that the fluorescent light is weak due to an excessively high concentration (concentration quenching) occurs, the measurement can be finished.

As described above, also in this embodiment, the liquid height and concentration of the sample liquid 20 can be measured.

Seventh Embodiment

Figure 20:
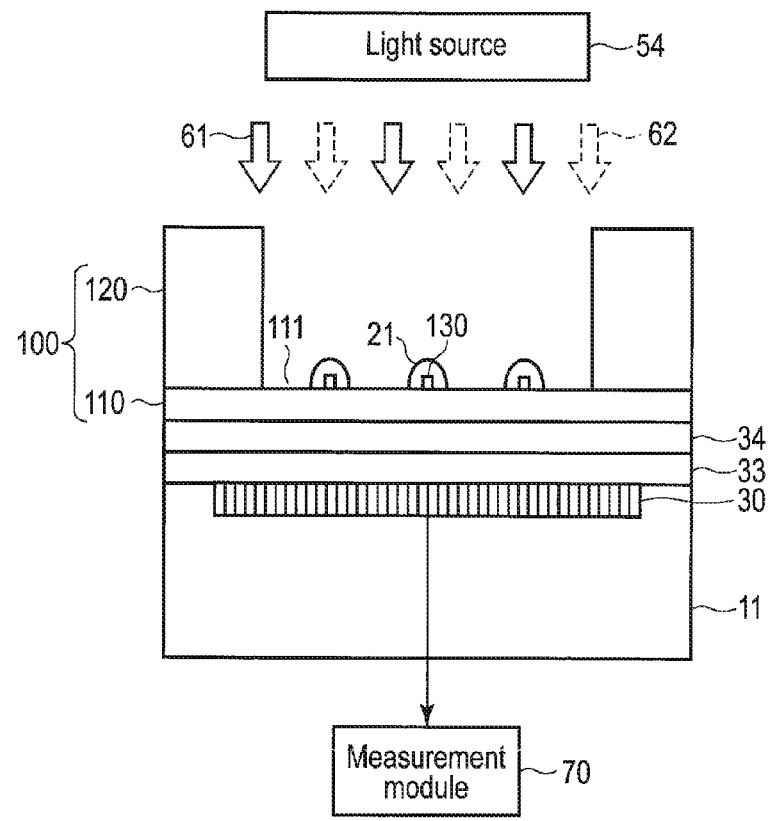
FIG. 20 is a schematic diagram showing a structure of a measuring device for a sample liquid according to the seventh embodiment.

FIG. 20 is a diagram schematically showing a structure of a sample liquid measuring device according to the seventh embodiment. Note that the same structural elements as those of FIG. 17 will be designated by the same reference symbols, and their detailed explanations will be omitted.

As in the case shown in FIG. 17, an optical sensor 30 which detects visible light and fluorescent light is provided on a substrate 11. The optical sensor 30 is a two-dimensional optical sensor array in which pixels are two-dimensionally arranged. The optical sensor 30 is a CMOS or CCD image sensor produced as, for example, a semiconductor chip. On the optical sensor 30, an optical filter 34 is provided via a protective insulating layer 33. On the optical filter 34, a container 100 to store sample liquid is provided.

The container 100 comprises a flat bottom wall 110 and rectangular or circular frame-shaped side walls 120. The container 100 is formed of, for example, polydimethylsiloxane (PDMS).

The bottom wall 110 is a transparent or translucent optical component comprising a water-repellent surface (a bottom surface of the container) to be brought into contact with the sample liquid. The surface 111 of the bottom wall 110 is subjected to, for example, a process with hexamethyldisilane (HMDS) to be water repellent. For the material of the bottom wall 110, a water-repellent material such as PDMS is preferable. Note here that the material is not necessarily limited to PDMS, but other moldable materials such as plastics or organic materials can be employed as well. Further, the surface can be coated with a para-xylene polymer or an inorganic material such as $SiO_2$ or $TiO_2$, as a structure of the embodiment. If sufficient water repellence is not obtained with these materials, then the surface should be subjected to an HMDS treatment or the like, to be water-repellent.

At least one pinning pattern 130 is formed on the surface 111 of the bottom wall 110. The pinning pattern 130 contributes to localization of the sample liquid, and may be a minute projection or may have hydrophilic property. When a plurality of pinning patterns 130 is to be provided, they should be arranged periodically.

Figure 21A:
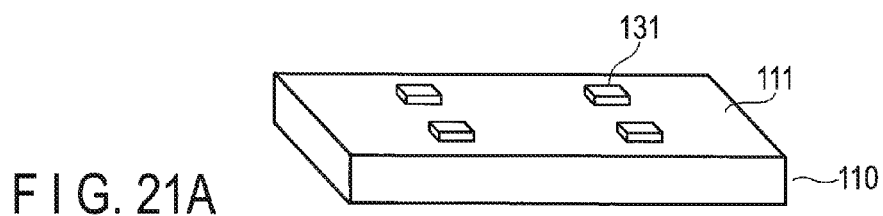
FIGS. 21A and 21B are perspective views each showing an example in which fine projections or hydrophilic portions are provided on a surface of the bottom wall.

FIG. 21A shows an example in which circular or rectangular minute projections 131 are provided in a section of the surface 111 of the bottom wall 110. Such projections 131 function as pinning patterns to localize the sample liquid. The width of each projection 131 should be, for example, 10 to 50 µm, and the height thereof should be, for example, 1 to 5 µm. Moreover, metal patterns of Au or the like may be formed on upper surfaces of the projections 131 to make them hydrophilic.

Figure 21B:
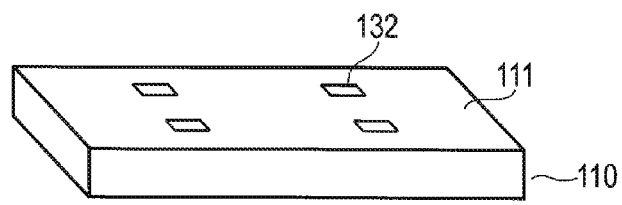

FIG. 21B shows an example in which the surface 111 of bottom wall 110 is partially treated with plasma in a circular or rectangular pattern so that the pattern should be hydrophilic.

Hydrophilic portions 132 function as pinning patterns to localize the sample liquid. In place of carrying out plasma treatment, metal patterns of Au or the like may be formed to prepare the hydrophilic portions 132.

In the plasma treatment to form hydrophilic portions, a resist is applied on a water-repellent surface and the resist is removed in the sections where hydrophilic portion are to be formed. Then, after exposing to plasma, the resist is peeled off. Moreover, in the formation of metal patterns, a metal film may be formed on the sections of the water-repellent surface, where the hydrophilic portions are to be formed, by a liftoff method. Or, after forming a metal film on the water-repellent surface, a resist pattern is formed so as to remain on the sections where the hydrophilic portions are to be formed. Then, the metal film is removed by etching using the resist pattern as the mask. After that, the resist is peeled off.

Note that in order to make the surface of the bottom wall 110 water-repellent, a water-repellent surface of periodic projections and recesses may be provided on the surface of the bottom wall of PDMS as shown in FIG. 22. More specifically, fine pillars 115 of PDMS each having a diameter 100 to 200 nmφ and a height of 300 to 500 nm may be arranged periodically at a pitch of 200 to 400 nm, and thus a super-water-repellent surface of a contact angle exceeding 150 degrees can be obtained.

Further, in the structure utilizing such periodic projections and recesses, regions 135 where no fine pillars are formed may be provided as shown in FIG. 23A, and thus such a structure can be formed, which is provided with pinning patterns in a part of the water-repellent surface. Furthermore, as shown in FIG. 23B, by forming some of the fine pillars 115 taller than others, a structure can be formed, which is provided with the projections 136 in a part of the water-repellent surface. Even with such manners, such a structure as that shown in FIG. 21A or 21B can be realized, which is provided with pinning patterns in a part of the water-repellent surface.

A light source 54 is configured to be able to vary the wavelength of its light emission as in the case of the sixth embodiment. For example, the light source 54 can switch between excitation light 61 and collimated light (for example, visible light) 62 of a wavelength different from that of the excitation light 61 in its light emission. The optical sensor 30 can detect the wavelengths of both the fluorescence by irradiation of the excitation light 61 and the collimated light 62.

With such structures, when a sample liquid 20 is dropped in the container 100 and then evaporated, the sample liquid 20 is condensed and localized to the pinning patterns 130. That is, droplets 21 of the sample liquid 20 are created on the pinning patterns 130.

Figure 24:
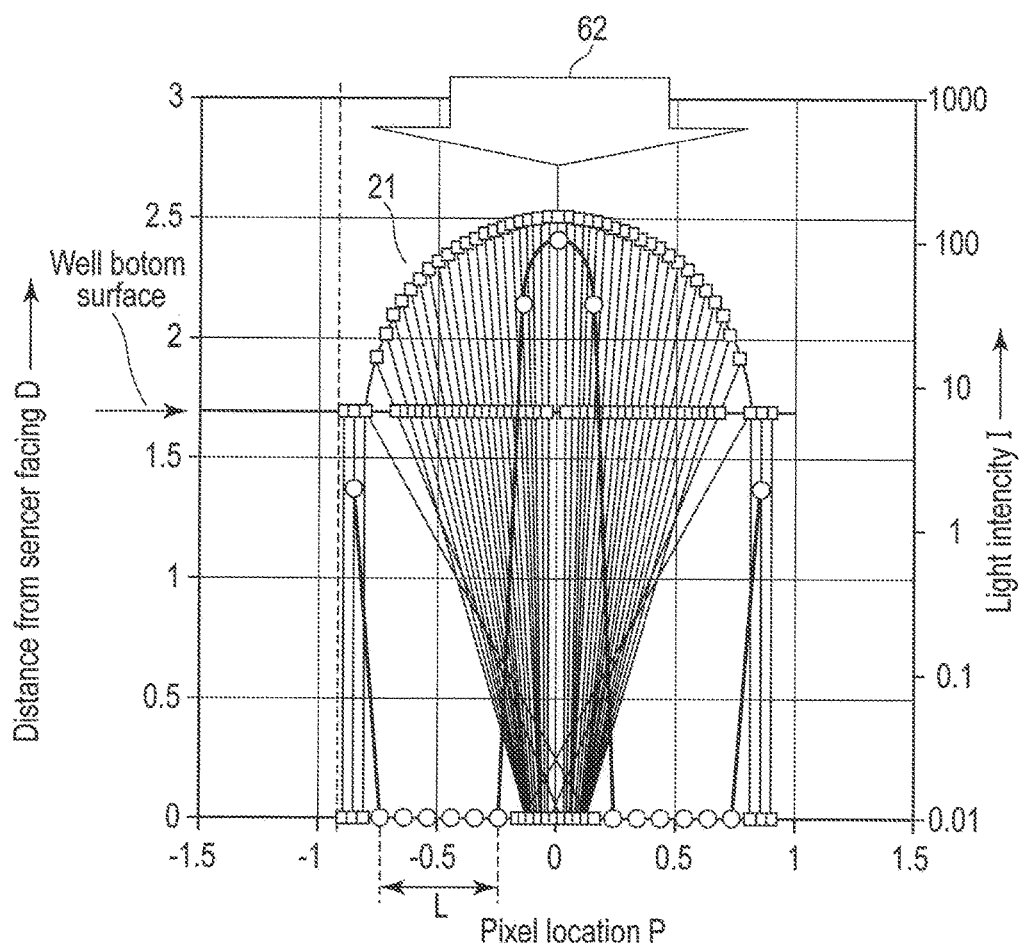
FIG. 24 is a schematic diagram showing how light is refracted by an interface of a droplet.

When the pinning patterns 130 are irradiated with the collimated light 62 while the minute droplets 21 are localized, the light is refracted on the interface of each droplet 21 as illustrated in FIG. 24. For this reason, the intensity of the light varies depending on the two-dimensional position on the sensor facing.

Figure 25:
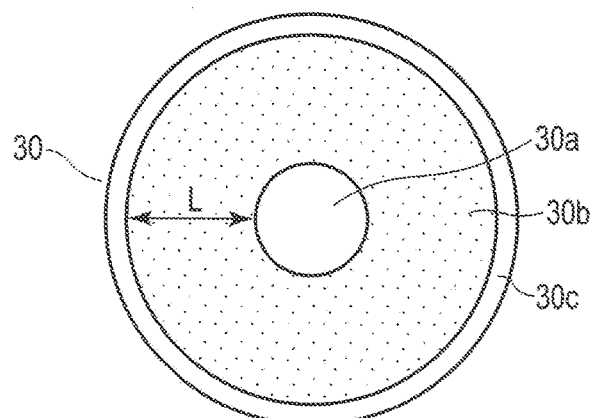
FIG. 25 is a schematic diagram showing the brightness of the light on a sensor facing.

More specifically, as shown in FIG. 25, a central portion 30a of the optical sensor 30 is very bright, the surrounding thereof creates a dark region 30b, and a further outer surrounding creates a bright region 30c. Thereby, a ring-like optical image is obtained. Note here that a width (doughnut width) L of the dark region 30b varies with the volume of the droplet 21.

Figure 26A:
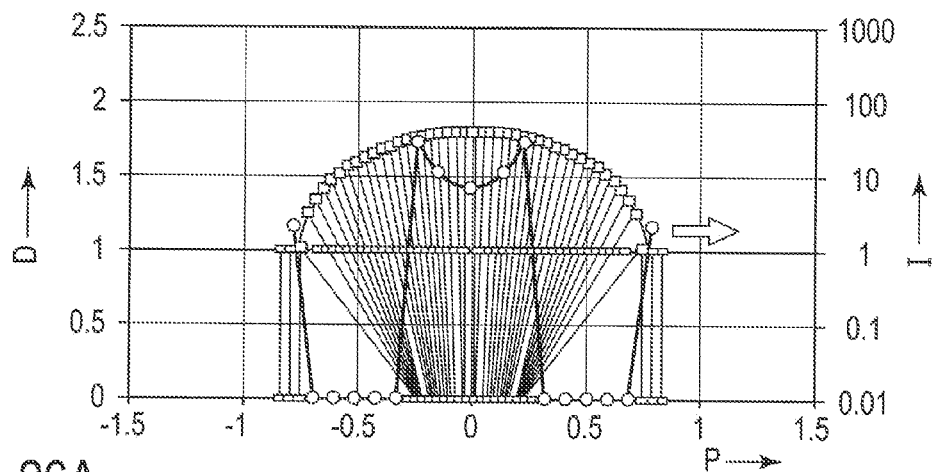
FIGS. 26A to 26C are schematic diagrams showing the relationship between the volume of droplet and the brightness at the sensor facing.
Figure 26B:
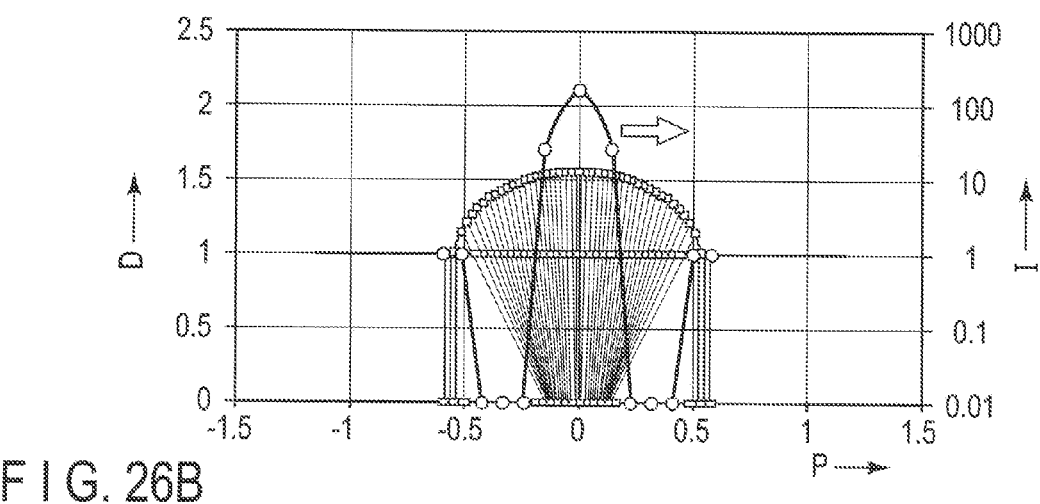
Figure 26C:
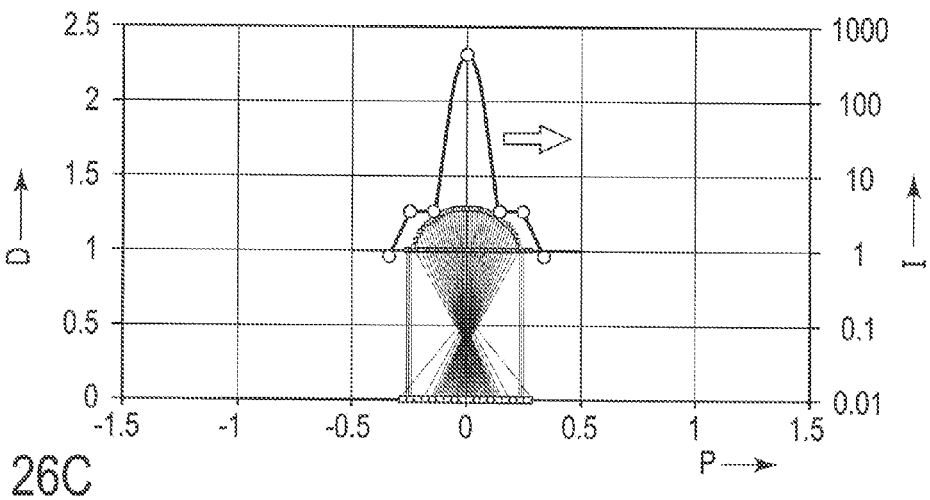

More specifically, as shown in FIGS. 26A to 26C, as the volume of the droplet 21 becomes smaller by condensation due to evaporation, the doughnut width L decreases, and when the volume of the droplet 21 becomes a certain level or below, the doughnut width L disappears. Based on this, it is possible to measure the volume (fluid volume) of the droplet 21 from the doughnut width L. In other words, the volume of the droplet 21 can be measured by analyzing the ring-like optical image using the optical model regarding the volume of droplet. Furthermore, since the volume of the droplet 21 is proportional to the height of the droplet 21, it is also possible to measure the height of the droplet 21.

Here, in the measurement of the volume of the droplet 21 from the doughnut width L, the distance between the bottom surface of the container 100 and the sensor facing is important. If the distance is excessively close, the variation of the doughnut width L to the change in volume becomes small, thereby making it difficult to achieve accurate measurement. On the other hand, if the distance is excessively far, the doughnut disappears as shown in FIG. 26C, thereby making it impossible to measure. For this reason, it is necessary to make the total thickness of the optical component (bottom wall 110), the insulating layer 33 and the filter 34 sufficiently thin in such a range that enables accurate measurement.

In addition, after the droplet evaporated completely and the sample deposited, the sample liquid does not take a sagittal shape unlike the droplet 21. Therefore, the volume of the sample liquid cannot be measured by a method using the optical analysis. In this case, the volume can be estimated by the following technique.

That is, first, a reference sample is created and the amount of fluorescence and volume thereof are obtained. More specifically, a liquid (sample liquid as a reference sample) same as the sample liquid to be measured is dropped on the bottom wall 110 in somewhat a great amount to such an extent that a sagittal form is created even after evaporation. Then, the sample liquid is evaporated to deposit the sample in a sagittal shape. Subsequently, a volume V0 and an amount P0 of fluorescence of the sample liquid which deposited in a sagittal shape are measured. The volume V0 is calculated from the shape of the sample liquid or mass (density) using a measuring device separately, and the amount P0 of fluorescence is calculated with the optical sensor 30.

Subsequently, the amount of fluorescence of the sample, that is, the sample liquid to be measured is measured and compared with the result of the reference sample, thereby obtaining the volume after evaporation. More specifically, only a predetermined amount of the sample liquid to be measured is dropped on the low wall portion 110, and then evaporated and deposited. An amount P2 of fluorescence at this time is measured with the optical sensor 30. A volume V2 of the sample liquid after deposition can be calculated from $V2=(P2/P0) \times V0$. The reference sample and the sample may be measured with the same measuring device, or separate measuring devices.

As in the sixth embodiment, this embodiment is able to detect the concentration of the droplet 21 by applying the excitation light 61 to the sample and detecting the fluorescence from the droplet 21 with the optical sensor.

Thus, in this embodiment, the volume (fluid volume) of the droplet 21 can be measured by irradiation of the collimated light 62, and the concentration of the droplet 21 can be measured by irradiation of the excitation light 61. Here, since the pinning patterns 130 such as a projections and hydrophilic portions are formed in a section of the water-repellent surface, the droplet 21 can be localized certainly at each pinning pattern 130, thereby making it possible to improve the reliability and accuracy of the test.

Further, no complicated processing is required to localize the sample liquid 20, but only with a structure of preparing projections and hydrophilic portions in a section of the water-repellent surface, the advantageous effect of the embodiment can be obtained.

FIGS. 27A to 27D are cross sections showing a process of manufacturing the measuring device of this embodiment.

First, on the substrate 11, those components up to the optical filter 34 are formed in advance. That is, the optical sensor 30 is formed on the substrate 11, and the protective insulating layer 33 and the optical filter 34 are formed thereon in advance (see FIG. 27A).

On the other hand, a mold 200 comprising recess portions for the patterns of the container 100 and the pinning patterns 130 is prepared. More specifically, the mold 200 is prepared, in which a recess portion 110a corresponding to the bottom wall 110 of the container 100, recess portions 120a corresponding to the side walls 120 and recess portions 130a corresponding to the pinning patterns 130 are formed (see FIG. 27B).

Then, PDMS 150 is dropped into the recess portions of the mold 200 to fill the recess with the PDMS 150. After that, the PDMS 150 is hardened by, for example, heat. Thus, the container 100 formed from PDMS is manufactured (see FIG. 27C).

Subsequently, the mold 200 in which the container 100 of PDMS is formed is overturned with the recess facing downward and adhered to the optical filter 34 on the substrate 11 (see FIG. 27D).

After that, the mold 200 is removed from the container 100 and thus the measuring device as shown in FIG. 20 is obtained.

(Modification)

Note that the embodiments are not limited to those discussed above.

The material of the optical component provided in the container can be changed as needed according to the specification. In the first and second embodiments, the material should just be transparent or translucent. In the third to sixth embodiments, the material should just be transparent or translucent and have a refractive index different from that of the sample liquid.

The optical sensor may not necessarily be formed to use its substrate as the bottom wall of the container, but in the case of the container which includes the bottom wall formed of a transparent material, the optical sensor may be installed so as to be in contact with the undersurface of the bottom wall of the container on the outer side thereof. In this case, it is desirable that the refractive index of the bottom wall of the container be the same as that of the optical component.

The optical sensor may not necessarily be a two-dimensional sensor such as an array sensor, but may be a one-dimensional sensor such as a line sensor.

Moreover, if the specific substance in the sample liquid is not a fluorophore but a luminous body, the light source for excitation can be omitted. In this case, the optical sensor should just be of a type which can detect luminescence from the specific substance in the sample liquid.

Each of the fourth and sixth embodiments discusses a structure in which the light is applied from a perpendicular direction, mainly, whereas the fifth embodiment discusses a structure in which light is applied from a horizontal direction, mainly. It is only natural that if the light is applied from an oblique direction, an advantageous effect similar to those of the fourth to sixth embodiments can be obtained by carrying out a process similar to those of these embodiments. Therefore, the relationship in position between the light source, optical component and optical sensor is not limited to the angles discussed in the embodiments but can be changed as needed.

Moreover, the method of measurement the sample liquid, which can support all of the embodiments, should only be configured as follows. That is, a sample liquid in a container is irradiated with light, and the light refracted by the interface of the sample liquid is detected in a lower portion of the container with an optical sensor. From the detected signal of the optical sensor, the liquid height and fluid volume of the sample liquid or the concentration of a specific substance contained in the sample liquid is measured.

Furthermore, the method of measuring the sample liquid, which supports the seventh embodiment should only be configured as follows. That is, a measuring device for measuring a sample liquid, which includes a container for storing the sample liquid; a transparent or translucent optical component provided as a bottom of the container, comprising a surface to be brought into contact with the liquid, which is water-repellent, the water-repellent surface further comprising at least one projection or hydrophilic portion, an optical sensor provided at a predetermined distance away from the surface of the bottom of the above-mentioned container, which is to be brought into contact with the sample liquid and configured to detect the light from the sample liquid; and a measurement module which measures the volume of the sample liquid localized in the projection or hydrophilic portion based on a detected signal of the optical sensor, is employed. The sample liquid is stored in the container and then evaporated therein to localize as a droplet on the projection or the hydrophilic portion. After localization of the sample liquid, light is applied from above the container to obtain a ring-like optical image with the optical sensor, and the image is measured with the measuring module, and the ring-like optical image is analyzed using an optical model regarding the volume of droplet to measure the volume of the droplet.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A measuring device for a sample liquid comprising:
   a container which stores the sample liquid, the container comprising a transparent or translucent optical inclined surface to be brought into contact with the sample liquid;
   an optical sensor provided on a bottom of the container and configured to detect a profile of intensity of light from the sample liquid; and
   a measurement processor configured to measure a liquid height of the sample liquid based on a profile of intensity of a detected signal of the optical sensor,
   wherein the transparent or translucent optical inclined surface comprises a lower end disposed within outer edges of the optical sensor.

2. The device of claim 1, further comprising:
   a light source provided above the container, which irradiates light to the sample liquid in the container.

3. The device of claim 1, wherein
   The transparent or translucent optical inclined surface has a ring shape and the transparent or translucent optical inclined surface expands upwards on an inner circumferential surface of the ring shape.

4. The device of claim 2, wherein
   the light source irradiates excitation light which excites a specific substance in the sample liquid to generate fluorescence, and
   the optical sensor detects the fluorescence from the sample liquid.

5. The device of claim 1, wherein
   the measurement processor calculates out a concentration of a specific substance contained in the sample liquid from the intensity of the detected signal, or obtains a liquid volume of the sample liquid from the profile of the intensity of the detected signal.

6. The device of claim 1, wherein
   the measurement processor measures a concentration of a specific substance contained in the sample liquid from a relationship between an intensity of the detected signal and the liquid height or the fluid volume.

7. The device of claim 1, wherein
the measurement processor obtains a relationship between the liquid height and an intensity of the detected signal, and measures near the liquid height where the intensity of the detected signal is at maximum.

8. The device of claim 1, further comprising:
an inlet mechanism which introduces a gas and an outlet mechanism which discharge the gas, provided above the container.

9. The device of claim 1, wherein
the transparent or translucent optical inclined surface has a shape of a triangular prism of a right triangle and includes two side surfaces perpendicular to each other, which are brought into contact with the bottom and a side of the container, and another side surface to be brought into contact with the sample liquid.

10. The device of claim 9, wherein
the transparent or translucent optical inclined surface has a refractive index different from that of the sample liquid.

11. The device of claim 10, wherein
the light is irradiated on the sample liquid in the container in an entire surface thereof from a perpendicular or horizontal direction, and the liquid height of the sample liquid is measured from a gradation of detected signals of the optical sensor.

12. The device of claim 10, wherein
the light is spot-irradiated into the sample liquid in the container from a perpendicular or horizontal direction, and the liquid height is measured from a shape of a spot image obtained by the optical sensor.

13. The device of claim 1, further comprising:
a light source which applies excitation light into the sample liquid in the container to cause generation of fluorescence,
wherein
the transparent or translucent optical inclined surface is provided as a part of the container and has a ring shape, and the inclined surface of the transparent or translucent optical inclined plane expands upwards on an inner circumferential surface of the ring shape, the inner circumferential surface being brought into contact with the sample liquid,
the optical sensor detects the fluorescence from the sample liquid, and
the measurement processor measures a concentration of a specific substance in the sample liquid based on a detected signal of the optical sensor.

14. A measuring device for a sample liquid comprising:
a container configured to stores the sample liquid;
an optical inclined surface provided on a side portion in the container, formed from a transparent or translucent material having a refractive index different from that of the sample liquid, and including an inclined surface at an angle less than 90 degrees with respect to a bottom of the container, the optical inclined surface being configured to be brought into contact with the sample liquid;
a light source which irradiates light into the container;
an optical sensor provided on a bottom of the container and configured to detect a profile of intensity of light from the sample liquid; and
a measurement processor which measures a liquid height of the sample liquid based on a profile of intensity of a detection signal of the optical sensor,
wherein the optical inclined surface comprises a lower end disposed within outer edges of the optical sensor.

15. The device of claim 14, wherein
the light source irradiates light into the container from a first direction, which is a horizontal direction, or from a vertical direction, and
the optical sensor is provided on a bottom of the container along the first direction.

16. The device of claim 14, wherein
the optical inclined surface has a shape of a triangular prism of a right triangle and includes two side surfaces perpendicular to each other, which are brought into contact with the bottom and a side of the container, and another side surface to be brought into contact with the sample liquid.

17. The device of claim 14, wherein
the light source irradiates collimated lights of a single wavelength on the sample liquid in its entire surface, and the liquid height is measured from a gradation of detected signals of the optical sensor.

18. The device of claim 14, wherein
the light source irradiates collimated lights of a single wavelength on the sample liquid in a spotted manner, and the liquid height is measured from a shape of a spot image obtained by the optical sensor.

19. The device of claim 14, wherein
the light source is configured to switch the wavelength of emission light.

20. A method of measuring a sample liquid, comprising:
irradiating the sample liquid in a container with light, the container comprising a transparent or translucent optical inclined surface that is brought into contact with the sample liquid;
detecting a profile of intensity of the light refracted by an interface of the sample liquid in a lower portion of the container with an optical sensor provided on a bottom of the container; and
measuring a liquid height of the sample liquid based on a profile of intensity of a detected signal of the optical sensor,
wherein the transparent or translucent optical inclined surface comprises a lower end disposed within outer edges of the optical sensor.

* * * * *